(12) United States Patent
Matsumura et al.

(10) Patent No.: US 10,280,412 B2
(45) Date of Patent: May 7, 2019

(54) METHOD FOR USING HEAT-RESISTANT MISMATCH ENDONUCLEASE

(71) Applicant: TAKARA BIO INC., Kusatsu-shi, Shiga (JP)

(72) Inventors: Kiyoyuki Matsumura, Otsu (JP); Nariaki Takatsu, Kusatsu (JP); Takashi Uemori, Otsu (JP); Hiroyuki Mukai, Beijing (CN)

(73) Assignee: TAKARA BIO INC., Shiga (JP)

( * ) Notice: Subject to any disclaimer, the term of this patent is extended or adjusted under 35 U.S.C. 154(b) by 0 days.

(21) Appl. No.: 16/217,581

(22) Filed: Dec. 12, 2018

(65) Prior Publication Data

US 2019/0100736 A1 Apr. 4, 2019

Related U.S. Application Data

(62) Division of application No. 16/142,717, filed on Sep. 26, 2018, which is a division of application No. 14/773,915, filed as application No. PCT/JP2014/056738 on Mar. 13, 2014, now Pat. No. 10,131,890.

(30) Foreign Application Priority Data

Mar. 14, 2013 (JP) ................................ 2013-052265

(51) Int. Cl.
  *C12N 9/22* (2006.01)
  *C12Q 1/683* (2018.01)
  *C12P 19/34* (2006.01)

(52) U.S. Cl.
  CPC ............... *C12N 9/22* (2013.01); *C12P 19/34* (2013.01); *C12Q 1/683* (2013.01); *C12Y 301/21* (2013.01)

(58) Field of Classification Search
  None
  See application file for complete search history.

(56) References Cited

U.S. PATENT DOCUMENTS

| | | |
|---|---|---|
| 5,922,539 A | 7/1999 | Modrich et al. |
| 6,391,557 B1 | 5/2002 | Yeung |
| 2003/0148283 A1 | 8/2003 | Barany |
| 2003/0165898 A1 | 9/2003 | Todd |
| 2004/0137451 A1 | 7/2004 | Sagawa et al. |
| 2006/0110765 A1 | 5/2006 | Wang |
| 2006/0248617 A1 | 11/2006 | Imanaka et al. |
| 2010/0055742 A1 | 3/2010 | Nakashima et al. |
| 2013/0149695 A1 | 6/2013 | Lee et al. |
| 2016/0017300 A1 | 1/2016 | Matsumura et al. |
| 2017/0253909 A1 | 9/2017 | Uemori et al. |
| 2018/0163263 A1 | 6/2018 | Uemori et al. |

FOREIGN PATENT DOCUMENTS

| | | |
|---|---|---|
| JP | 2000-511774 | 9/2000 |
| JP | 2003-518951 | 6/2003 |
| JP | 2004-526423 | 9/2004 |
| JP | 2007-295838 | 11/2007 |
| JP | 2007-319096 | 12/2007 |
| JP | 2008-48725 | 3/2008 |
| JP | 2008-520245 | 6/2008 |
| WO | 96/32500 | 10/1996 |
| WO | 97/46701 | 12/1997 |
| WO | 99/42595 | 8/1999 |
| WO | 00/56929 | 9/2000 |
| WO | 01/49877 | 7/2001 |
| WO | 01/62974 | 8/2001 |
| WO | 02/44335 | 6/2002 |
| WO | 03/048395 | 6/2003 |
| WO | 2013/175815 | 11/2003 |
| WO | 2004/022736 | 3/2004 |
| WO | 2011/102802 | 8/2011 |
| WO | 2013/116771 | 8/2013 |
| WO | 2014/142261 | 9/2014 |
| WO | 2016/039377 | 3/2016 |

OTHER PUBLICATIONS

Extended European Search Report dated Sep. 17, 2018 in corresponding European patent application No. 16768715.1.
Extended European Search Report dated Feb. 12, 2018 issued in corresponding European patent application No. 15839690.03.
Nishioka et al., "Characterization of two intein homing endonucleases encoded in the DNA polymerase gene of Phyrococcus kodakaraensis strain KOD1", Nucleic Acids Research, 1998, vol. 26. No. 19, pp. 4409-4412.
Mean et al., "Modification of the enzyme mismatch cleavage method using T7 endonuclease I and silver staining", BioTechniques, 2004, vol. 36, No. 5, p. 758-760.
Qiu, et al., "Mutation detection using SurveyorTM nuclease", BioTechniques, 2004, vol. 36, No. 4, p. 702-707.
Office Action dated Nov. 17, 2015 in corresponding Japanese Application No. 2015-505565, with English translation.
Kari et al., "Generation of targeted *Chlamydia trachomatis* null mutants", PNAS, vol. 108, No. 17, Apr. 26, 2011, pp. 7189-7193.
Smith et al., "Mutation detection with MutH, MutL, and MutS mismatch repair proteins", Proc. Natl. Acad. Sci. USA, vol. 93, Apr. 1996, pp. 4374-4379.
Bridger et al., Database Uniprot [online], Accession No. I6U8Z8, uploaded Oct. 3, 2012, 1 page.

(Continued)

*Primary Examiner* — Manjunath N Rao
*Assistant Examiner* — Jae W Lee
(74) *Attorney, Agent, or Firm* — Wenderoth, Lind & Ponack, L.L.P.

(57) ABSTRACT

Provided are a mismatch-specific cleavage reaction using a novel heat-resistant mismatch nuclease, a method for removing errors in a nucleic acid amplification reaction using the mismatch nuclease, a method for inhibiting the amplification of a nucleic acid having a specific base sequence during a nucleic acid amplification reaction, and a method for detecting a nucleic acid having a single-base polymorphic mutation using this inhibition method.

6 Claims, 6 Drawing Sheets

Specification includes a Sequence Listing.

(56) References Cited

OTHER PUBLICATIONS

Maeder et al., Database Uniprot [online], Accession No. Q8U4R1, uploaded Jun. 1, 2002, 2 pages.
Zhulidov et al., "Simple cDNA normalization using kamchatka crab duplex-specific nuclease", Nucleic Acids Research, vol. 32, No. 3, 2004, e37, pp. 1-8.
Hillmann et al., "cDNA Amplification by SMART-PCR and Suppression Subtractive Hybridization (SSH)-PCR", DNA and RNA Profiling in Human Blood: Methods and Protocols, vol. 496, No. 2, Chapter 15, 2009, 223-243.
Ward et al., "Restriction Endonuclease-Mediated Selective Polymerase Chain Reaction", American Journal of Pathology, vol. 153, No. 2, Aug. 1998, pp. 373-379.
International Search Report dated May 20, 2014 in International (PCT) Application No. PCT/JP2014/056738.
Office Action dated Sep. 6, 2017 issued in corresponding European Patent Application No. 14765697.2.
Todd et al., "Allele-specific Enrichment: A Method for the Detection of Low Level N-ras Gene Mutations in Acute Myeloid Leukemia", Leukemia, Feb. 1991, vol. 5, No. 2, pp. 160-161.
Kahn et al., "Rapid and sensitive nonradioactive detection of mutant K-ras genes via 'enriched' PCR amplification", Oncogene, 1991, vol. 6, No. 6, pp. 1079-1083.
Lee et al., "Mutant Enrichment with 3'-Modified Oligonucleotides a Practical PCR Method for Detecting Trace Mutant DNAs", The Journal of Molecular Diagnostices, Nov. 2011, vol. 13, No. 6, pp. 657-668.
English translation of the International Application No. PCT/JP2016/058852. Preliminary Report on Patentability dated Oct. 5, 2017 in corresponding PCT Application No. PCT/JP2016/058852.
English translation of the International Search Report dated Jun. 14, 2016 in corresponding PCT Application No. PCT/JP2013/058852.
Office Action dated Dec. 30, 2016 in corresponding Chinese Application No. 201480026443.6, with English translation.
Dongmei et al., "Correction of the Error in Chemical DNA Synthesis", Chemistry of Life, vol. 32, No. 1, (2012), pp. 34-38, with English translation.
Sonoko Ishino et al., "Identification of a mismatch-specific endonuclease in hyperthermophilic Archaea", Nucleic Acids Research, vol. 44, No. 7, 2016, pp. 2977-2986.
Extended European Search Report dated Oct. 27, 2016 in corresponding European Application No. 14762697.2.
International Preliminary Report on Patentability dated Mar. 14, 2017 issued in International Patent Application No. PCT/JP2015/075603.
RecName: Full=Endonuclease NucS, Database NCBI Protein [online], May 14, 2014, Accession No. Q5JER9, 2 pages.
Yumani Kuba et al., "Comparative analyses of the two proliferating cell nuclear antigens from the hyperthermophilic archaeon, Thermococcus kodakarensis", Genes to Cells, 2012, vol. 17, No. 11, pp. 923-937.
International Search Report dated Oct. 13, 2015 issued in International Patent Application No. PCT/JP2015/075603.
Japanese Office Action dated Apr. 25, 2017 issued in corresponding Japanese Patent Application No. 2016-129036 (with Machine English Translation).
Accession No. FOLKL8, Uniprot[online], Feb. 6, 2013, retrieved on Apr. 12, 2017, URL: http://www.uniprot.org/uniprot/FOLKL8.txt?version=12, 2 pages.
Accession No. Q57678, Uniprot[online], Nov. 28, 2012, retrieved on Apr. 12, 2017, URL: http://www.uniprot.org/uniprot/Q57678.txt?version=62, 2 pages.
Pauline Vannier et al., "Complete Genome Sequence of the Hyperthermophilic, Piezophilic, Heterotrophic, and Carboxydotrophic Archaeon *Thermococcus barophilus* MP", Journal of Bacteriology, 2011, vol. 193, No. 6, pp. 1481-1482.
Carol J. Bult et al., "Complete Genome Sequence of the Methanogenic Archaeon, *Methanococcus jannaschii*", Science, 1996, vol. 273, pp. 1058-1073.
Office Action dated Jan. 12, 2018 issued in U.S. Appl. No. 14/773,915.
International Preliminary Report on Patentability dated Sep. 15, 2015 in International (PCT) Application No. PCT/JP2014/056738.

[Fig.1]
a) ROX Detection
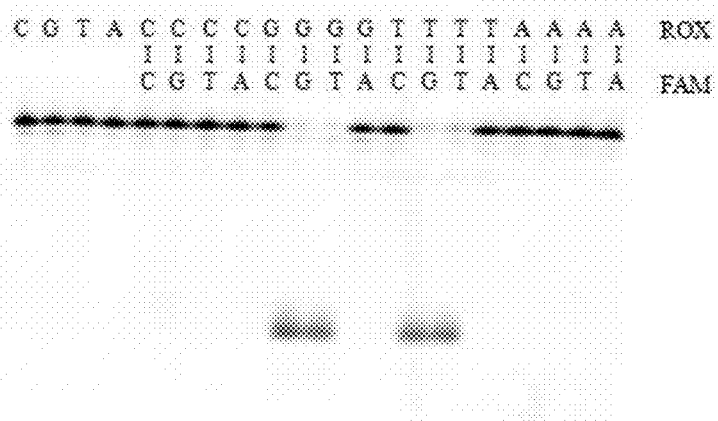
b) FAM Detection
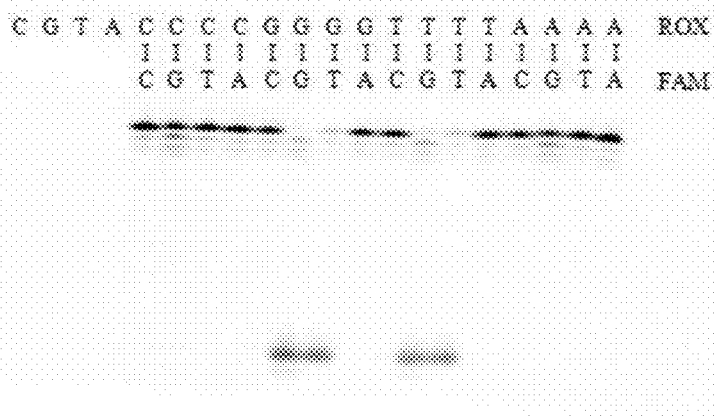

[Fig. 2]
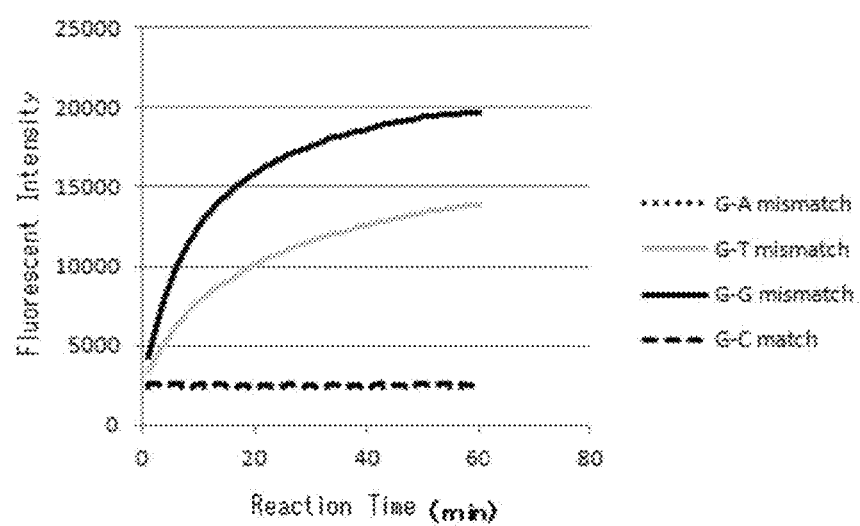

[Fig.3]
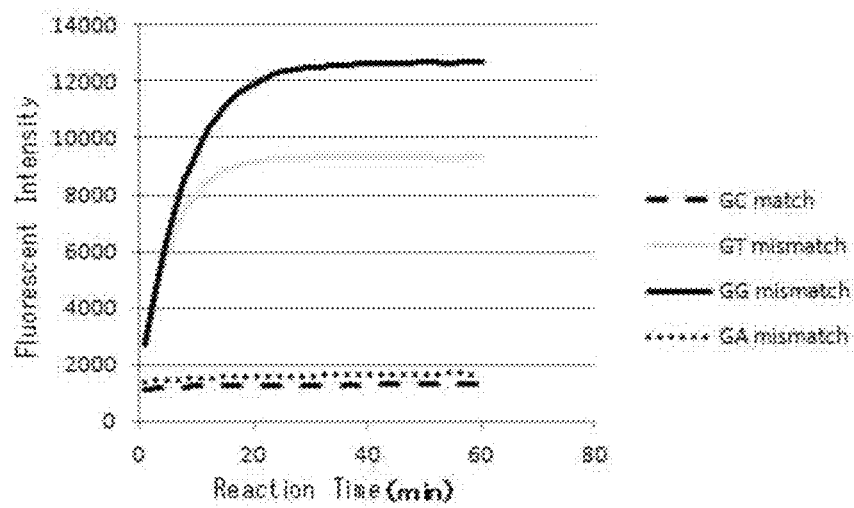
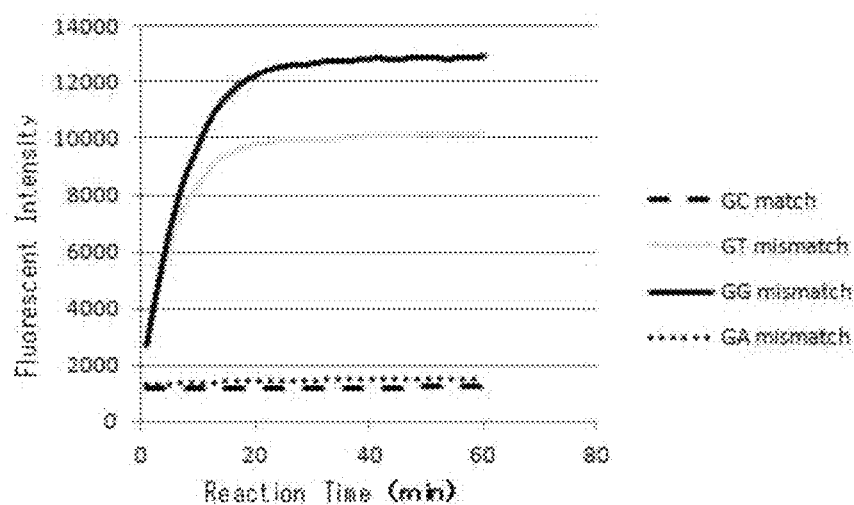

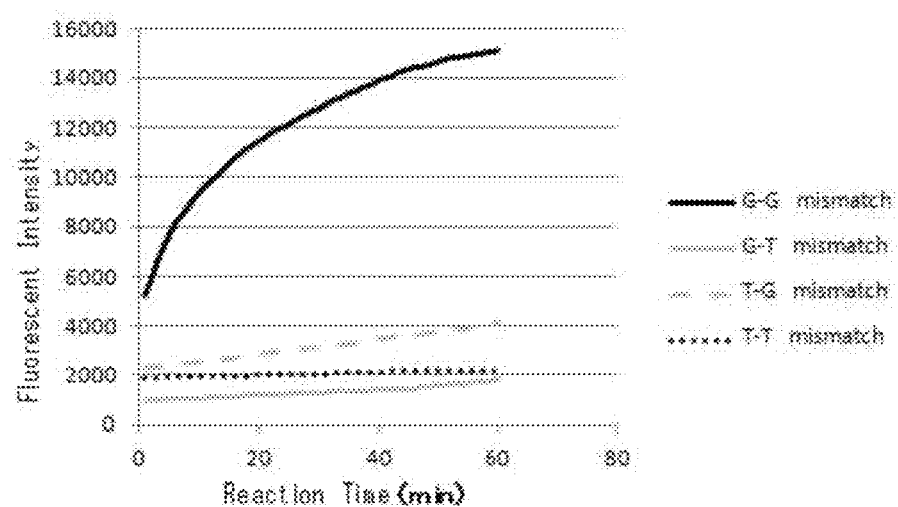
[Fig.4]

[Fig.5]
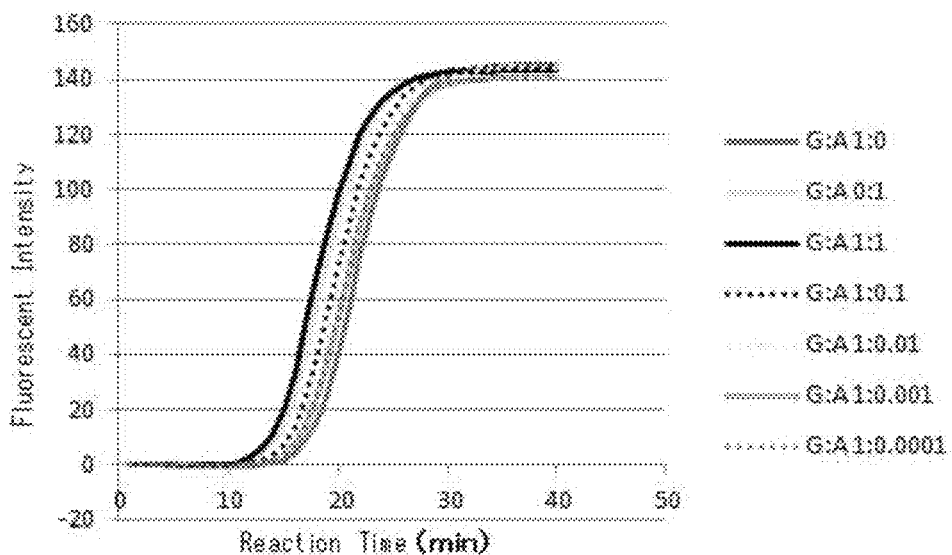
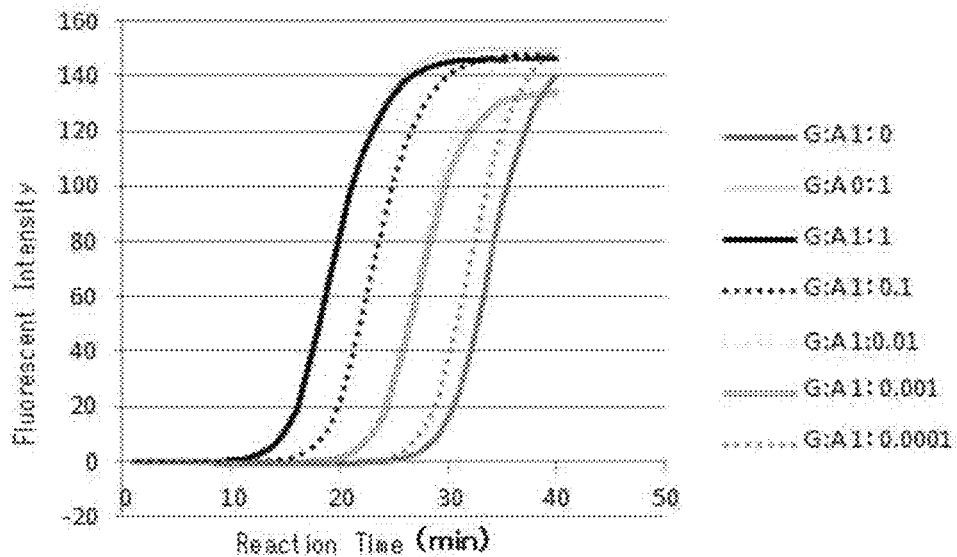

[Fig. 6]
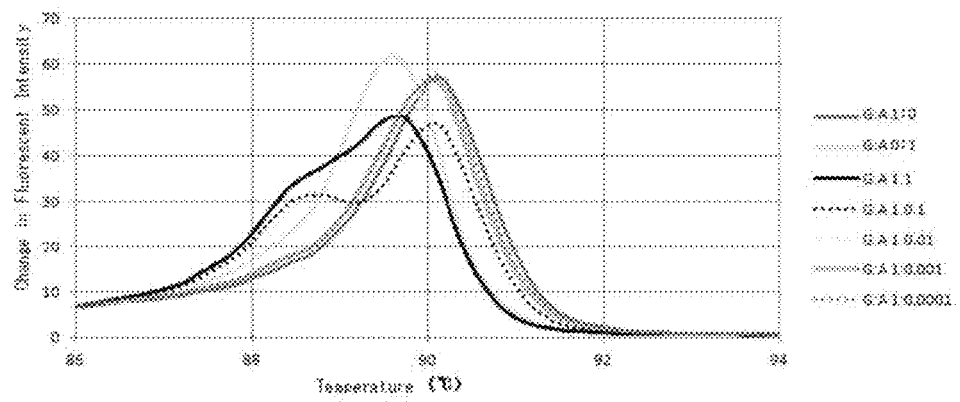
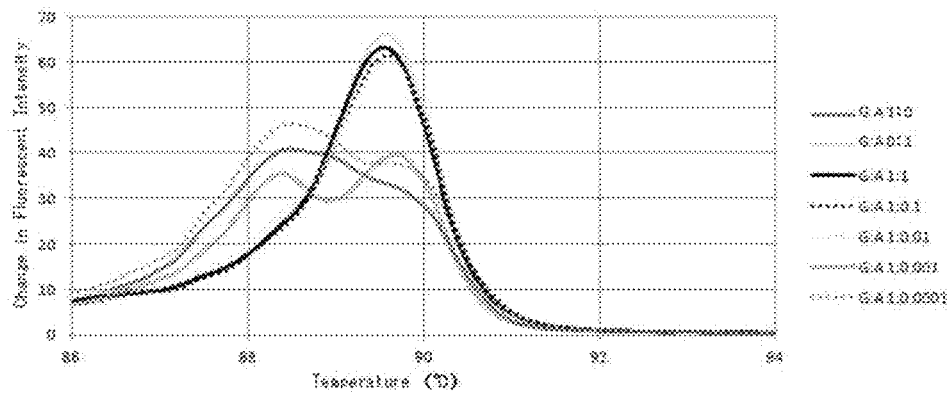

```
                        SEQUENCE LISTING

<160> NUMBER OF SEQ ID NOS: 46

<210> SEQ ID NO 1
<211> LENGTH: 267
<212> TYPE: PRT
<213> ORGANISM: Pyrococcus furiosus

<400> SEQUENCE: 1

Met Glu Met Thr Lys Ala Ile Val Lys Glu Asn Pro Arg Ile Glu Glu
1               5                   10                  15

Ile Lys Glu Leu Leu Glu Val Ala Glu Ser Arg Glu Gly Leu Leu Thr
            20                  25                  30

Ile Phe Ala Arg Cys Thr Val Tyr Tyr Glu Gly Arg Ala Lys Ser Glu
        35                  40                  45

Leu Gly Glu Gly Asp Arg Ile Ile Ile Lys Pro Asp Gly Ser Phe
    50                  55                  60

Leu Ile His Gln Lys Lys Lys Arg Glu Pro Val Asn Trp Gln Pro Pro
65                  70                  75                  80

Gly Ser Lys Val Lys Met Glu Gly Asn Ser Leu Ile Ser Ile Arg Arg
                85                  90                  95

Asn Pro Lys Glu Thr Leu Lys Val Asp Ile Ile Glu Ala Tyr Ala Ala
            100                 105                 110

Val Leu Phe Met Ala Glu Asp Tyr Glu Glu Leu Thr Leu Thr Gly Ser
        115                 120                 125

Glu Ala Glu Met Ala Glu Leu Ile Phe Gln Asn Pro Asn Val Ile Glu
    130                 135                 140

Glu Gly Phe Lys Pro Met Phe Arg Glu Lys Pro Ile Lys His Gly Ile
145                 150                 155                 160

Val Asp Val Leu Gly Val Asp Arg Glu Gly Asn Ile Val Val Leu Glu
                165                 170                 175

Leu Lys Arg Arg Arg Ala Asp Leu His Ala Val Ser Gln Leu Lys Arg
            180                 185                 190

Tyr Val Asp Ala Leu Lys Glu Glu His Gly Asn Lys Val Arg Gly Ile
        195                 200                 205

Leu Val Ala Pro Ser Leu Thr Glu Gly Ala Lys Lys Leu Leu Glu Lys
    210                 215                 220

Leu Gly Leu Glu Phe Arg Lys Leu Glu Pro Pro Lys Lys Gly Lys Lys
225                 230                 235                 240

Lys Ser Ser Lys Gln Lys Thr Leu Asp Phe Leu Asn Asp Thr Val Arg
                245                 250                 255

Ile Thr Gly Ala Ser Pro Pro Glu Ala Ile Gln
```

```
              260                 265

<210> SEQ ID NO 2
<211> LENGTH: 267
<212> TYPE: PRT
<213> ORGANISM: Pyrococcus furiosus

<400> SEQUENCE: 2

Met Glu Met Thr Lys Ala Ile Val Lys Glu Asn Pro Arg Ile Glu Glu
1               5                   10                  15

Ile Lys Glu Leu Leu Glu Val Ala Glu Ser Arg Glu Gly Leu Leu Thr
            20                  25                  30

Ile Phe Ala Arg Cys Thr Val Tyr Tyr Glu Gly Arg Ala Lys Ser Glu
        35                  40                  45

Leu Gly Glu Gly Asp Arg Ile Ile Ile Lys Pro Asp Gly Ser Phe
    50                  55                  60

Leu Ile His Gln Lys Lys Arg Glu Pro Val Asn Phe Gln Pro Pro
65                  70                  75                  80

Gly Ser Lys Val Lys Met Glu Gly Asn Ser Leu Ile Ser Ile Arg Arg
                85                  90                  95

Asn Pro Lys Glu Thr Leu Lys Val Asp Ile Ile Glu Ala Tyr Ala Ala
            100                 105                 110

Val Leu Phe Met Ala Glu Asp Tyr Glu Glu Leu Thr Leu Thr Gly Ser
        115                 120                 125

Glu Ala Glu Met Ala Glu Leu Ile Phe Gln Asn Pro Asn Val Ile Glu
    130                 135                 140

Glu Gly Phe Lys Pro Met Phe Arg Glu Lys Pro Ile Lys His Gly Ile
145                 150                 155                 160

Val Asp Val Leu Gly Val Asp Arg Glu Gly Asn Ile Val Val Leu Glu
                165                 170                 175

Leu Lys Arg Arg Arg Ala Asp Leu His Ala Val Ser Gln Leu Lys Arg
            180                 185                 190

Tyr Val Asp Ala Leu Lys Glu Glu His Gly Asn Lys Val Arg Gly Ile
        195                 200                 205

Leu Val Ala Pro Ser Leu Thr Glu Gly Ala Lys Lys Leu Leu Glu Lys
    210                 215                 220

Leu Gly Leu Glu Phe Arg Lys Leu Glu Pro Lys Lys Gly Lys Lys
225                 230                 235                 240

Lys Ser Ser Lys Gln Lys Thr Leu Asp Phe Leu Asn Asp Thr Val Arg
                245                 250                 255

Ile Thr Gly Ala Ser Pro Pro Glu Ala Ile Gln
            260                 265

<210> SEQ ID NO 3
<211> LENGTH: 36
<212> TYPE: DNA
<213> ORGANISM: Artificial Sequence
<220> FEATURE:
<223> OTHER INFORMATION: synthetic oligo nucleotide

<400> SEQUENCE: 3
cgcgcggcag ccatatggaa atgacgaaag caatag                        36

<210> SEQ ID NO 4
<211> LENGTH: 36
<212> TYPE: DNA
<213> ORGANISM: Artificial Sequence
<220> FEATURE:
```

<223> OTHER INFORMATION: synthetic oligo nucleotide

<400> SEQUENCE: 4
gttagcagcc ggatccttac tgaatggctt caggag         36

<210> SEQ ID NO 5
<211> LENGTH: 834
<212> TYPE: DNA
<213> ORGANISM: Pyrococcus furiosus

<400> SEQUENCE: 5

```
cgcgcggcag ccatatggaa atgacgaaag caatagtaaa agaaaatccc aggattgaag      60
agataaaaga gttattggaa gttgcagaga gtagggaagg gttacttaca atttttgcta     120
ggtgtaccgt ttattatgag ggaagggcca agagtgagct tggagaagga gacaggatta     180
taataataaa gcctgatgga agcttcctta tccaccagaa gaagaaaagg gagcctgtca     240
attggcaacc ccctgggagt aaagtaaaaa tggaaggaaa ctccttaatt agcattagaa     300
ggaacccaaa agaaacactc aaagttgata taattgaagc atatgcagca gttcttttca     360
tggcagagga ctatgaggag ctaaccctaa ctggaagtga agcagagatg gctgagctca     420
tttttccaaaa tcccaatgtt atcgaggaag gatttaaacc aatgtttaga gagaagccaa     480
taaagcatgg aatagttgat gtacttggcg tggacagaga gggaaatata gtagttctag     540
aactgaaaag gaggagggcc gatttacacg cggttagtca gttaagagg tacgtagatg       600
cactaaaaga agaacatgga aataaagtaa gaggaatatt ggtggcacct tctctaacgg     660
aaggagctaa aaagctttta gagaaacttg ggctagagtt tagaaagtta gaacctccta     720
aaaaaggtaa aagaaaagt tcaaagcaaa aaactctaga cttcctcaac gatactgtta     780
ggataactgg ggcatcacct cctgaagcca ttcagtaagg atccggctgc taac            834
```

<210> SEQ ID NO 6
<211> LENGTH: 813
<212> TYPE: DNA
<213> ORGANISM: Artificial Sequence
<220> FEATURE:
<223> OTHER INFORMATION: a designed sequence deduced from PF0012 amino
      acid sequence

<400> SEQUENCE: 6

```
catatggaaa tgaccaaagc gattgtgaaa gaaaacccgc gcattgaaga aattaaagaa      60
ctgctggaag tggcggaaag ccgcgaaggc ctgctgacca ttttttgcgcg ctgcaccgtg     120
tattatgaag gccgcgcgaa aagcgaactg ggcgaaggcg atcgcattat tattattaaa     180
ccggatggca gctttctgat tcatcagaaa aagaaacgcg aaccggtgaa ctggcagccg     240
ccgggcagca aagtgaaaat ggaaggcaac agcctgatta gcattcgccg caaccccgaaa     300
gaaaccctga agtggatat tattgaagcg tatgcggcgg tgctgtttat ggcggaagat     360
tatgaagaac tgaccctgac cggcagcgaa gcggaaatgg cggaactgat ttttcagaac     420
ccgaacgtga ttgaagaagg ctttaaaccg atgtttcgcg aaaaaccgat taaacatggc     480
attgtggatg tgctgggcgt ggatcgcgaa ggcaacattg tggtgctgga actgaaacgc     540
cgccgcgcgg atctgcatgc ggtgagccag ctgaaacgct atgtggatgc gctgaaagaa     600
gaacatggca acaaagtgcg cggcattctg gtggcgccga gcctgaccga aggcgcgaaa     660
aaactgctgg aaaaactggg cctggaattt gcaaactgg aaccgccgaa aaaaggcaaa     720
aagaaaagca gcaaacagaa aaccctggat tttctgaacg ataccgtgcg cattaccggc     780
``` gcgagccgc cggaagcgat tcagtaagga tcc 813

<210> SEQ ID NO 7
<211> LENGTH: 251
<212> TYPE: PRT
<213> ORGANISM: Thermococcus barophilus

<400> SEQUENCE: 7

```
Met Glu Ala Lys Val Glu Pro Ser His Glu Ile Ile Glu Ile Leu
1               5                   10                  15

Asp Lys Ala Leu Ser Val Glu Ala Ile Ile Thr Leu Phe Ala Tyr Cys
            20                  25                  30

Arg Val Phe Tyr Glu Gly Arg Ala Lys Ser Glu Leu Gly Pro Gly Asp
        35                  40                  45

Arg Val Ile Ile Ile Lys Pro Asp Gly Ser Phe Leu Ile His Gln Lys
    50                  55                  60

Asn Lys Arg Glu Pro Val Asn Trp Gln Pro Gly Ser Val Val Ser
65                  70                  75                  80

Ile Val Leu Glu Asp Gly Arg Ile Met Leu Arg Ser Val Arg Arg Lys
                85                  90                  95

Pro Lys Glu Thr Leu Glu Val Glu Leu Ile Lys Thr Tyr Leu Val Ser
            100                 105                 110

Tyr Phe Gln Ala Glu Asp Tyr Glu Glu Leu Thr Leu Thr Gly Ser Glu
        115                 120                 125

Ala Glu Met Ala Asp Leu Ile Phe Glu Asn Pro Ser Leu Ile Glu Glu
    130                 135                 140

Gly Phe Lys Pro Leu Phe Lys Glu Lys Pro Ile Lys His Gly Ile Val
145                 150                 155                 160

Asp Val Leu Gly Lys Asp Lys His Gly Asn Leu Val Val Leu Glu Leu
                165                 170                 175

Lys Arg Arg Arg Ala Asp Leu His Ala Val Ser Gln Leu Lys Arg Tyr
            180                 185                 190

Val Asp Ser Leu Arg Glu Glu His Lys Asn Val Arg Gly Ile Leu Val
        195                 200                 205

Ala Pro Ser Leu Thr Ala Gly Ala Lys Lys Leu Leu Lys Lys Glu Gly
    210                 215                 220

Leu Glu Phe Lys Lys Leu Asn Pro Pro Lys Arg Glu Lys Arg Lys Lys
225                 230                 235                 240

Gly Lys Gln Lys Thr Leu Asp Phe Leu Ser Pro
            245                 250
```

<210> SEQ ID NO 8
<211> LENGTH: 263
<212> TYPE: PRT
<213> ORGANISM: Methanocaldococcus jannaschii

<400> SEQUENCE: 8

```
Met Met Arg Leu Glu Lys Val Phe Tyr Leu Thr Asn Pro Thr Thr Lys
1               5                   10                  15

Asp Leu Glu Asn Phe Ile Asp Met Tyr Val Phe Lys Tyr Ile Leu Ile
            20                  25                  30

Leu Leu Ala Arg Cys Lys Val Phe Tyr Glu Gly Arg Ala Lys Ser Gln
        35                  40                  45

Leu Glu Glu Gly Asp Arg Val Ile Ile Ile Lys Pro Asp Gly Ala Phe
    50                  55                  60

Leu Ile His Lys Asp Lys Lys Arg Glu Pro Val Asn Trp Gln Pro Ser
```

```
            65                  70                  75                  80
    Gly Ser Ser Ile Ile Trp Glu Val Glu Asp Asn Phe Phe Ile Leu Lys
                    85                  90                  95

Ser Ile Arg Arg Lys Pro Lys Glu Glu Leu Lys Val Val Ile Ser Glu
                100                 105                 110

Val Tyr His Ala Cys Ala Phe Asn Cys Glu Asp Tyr Glu Glu Ile Asn
                115                 120                 125

Leu Arg Gly Ser Glu Ser Glu Met Ala Glu Met Ile Phe Arg Asn Pro
                130                 135                 140

Asp Leu Ile Glu Glu Gly Phe Lys Pro Ile Ser Arg Glu Tyr Gln Ile
    145                 150                 155                 160

Pro Thr Gly Ile Val Asp Ile Leu Gly Lys Asp Lys Glu Asn Lys Trp
                    165                 170                 175

Val Ile Leu Glu Leu Lys Arg Arg Arg Ala Asp Leu Gln Ala Val Ser
                180                 185                 190

Gln Leu Lys Arg Tyr Val Glu Tyr Phe Lys Asn Lys Tyr Gly Glu Asp
                195                 200                 205

Lys Val Arg Gly Ile Leu Val Ser Pro Ser Leu Thr Thr Gly Ala Glu
                210                 215                 220

Lys Leu Leu Lys Glu Glu Asn Leu Glu Phe Lys Arg Leu Asn Pro Pro
    225                 230                 235                 240

Lys Gly Ser Lys Arg Asp Leu Lys His Asn Ile Lys Thr Lys Lys Thr
                    245                 250                 255

Thr Val Leu Asp Glu Trp Leu
                260
```

<210> SEQ ID NO 9
<211> LENGTH: 37
<212> TYPE: DNA
<213> ORGANISM: Artificial Sequence
<220> FEATURE:
<223> OTHER INFORMATION: synthetic oligo nucleotide

<400> SEQUENCE: 9
cgcgcggcag ccatatggaa gctaaggttg aaccctc                        37

<210> SEQ ID NO 10
<211> LENGTH: 37
<212> TYPE: DNA
<213> ORGANISM: Artificial Sequence
<220> FEATURE:
<223> OTHER INFORMATION: synthetic oligo nucleotide

<400> SEQUENCE: 10
gttagcagcc ggatccctat gggctgagaa aatcaag                        37

<210> SEQ ID NO 11
<211> LENGTH: 38
<212> TYPE: DNA
<213> ORGANISM: Artificial Sequence
<220> FEATURE:
<223> OTHER INFORMATION: synthetic oligo nucleotide

<400> SEQUENCE: 11
cgcgcggcag ccatatgatg agattggaga agttttc                        38

<210> SEQ ID NO 12
<211> LENGTH: 39
<212> TYPE: DNA
<213> ORGANISM: Artificial Sequence

```
<220> FEATURE:
<223> OTHER INFORMATION: synthetic oligo nucleotide

<400> SEQUENCE: 12
gttagcagcc ggatccttat agccattcat ctaaaactg                            39

<210> SEQ ID NO 13
<211> LENGTH: 786
<212> TYPE: DNA
<213> ORGANISM: Thermococcus barophilus

<400> SEQUENCE: 13
cgcgcggcag ccatatggaa gctaaggttg aaccctctca cgaagaaata attgaaattt     60
tggataaagc cctctctgtt gaggctatca taactctttt tgcttattgt agggtattct    120
atgaggggag agccaagagt gagcttggcc ccggagatag ggtcattata atcaagccag    180
atggctcttt tttaattcac cagaagaaca aaagagaacc tgttaactgg cagccgccgg    240
ggagtgttgt cagcatcgtt cttgaggatg ggagaataat gctgagaagt gttaggagaa    300
aaccgaaaga aacccttgaa gttgagctca ttaaaactta tcttgtgagt tatttccaag    360
cagaggatta tgaggagctg acattaactg gaagtgaagc agagatggct gatttgatct    420
ttgagaatcc ctcattaatt gaggaaggat ttaaaccgct ctttaaggaa aagccaatta    480
aacatggaat agttgatgtg cttggaaaag acaaacatgg caatttggtt gtccttgagc    540
ttaagcgcag gagagcagat ctgcatgcgg tcagtcaact aaaagatat gttgattctc      600 tgagggagga gcataaaaat gttcgtggga ttttggttgc cccttctctt acggctgggg    660
ctaaaaaatt acttgaaaaa gaagggctgg aatttaaaaa gctgaatcca ccaaagcgtg    720
aaaagaggaa aaaaggcaag cagaaaaccc ttgattttct cagcccatag ggatccggct    780
gctaac                                                               786

<210> SEQ ID NO 14
<211> LENGTH: 822
<212> TYPE: DNA
<213> ORGANISM: Methanocaldococcus jannaschii

<400> SEQUENCE: 14
cgcgcggcag ccatatgatg agattggaga agttttctca tctaaccaat cctactacca     60
aagatttaga aaattttatt gatatgtatg tgtttaaata tatattaata ttattagctc    120
gatgtaaagt ttttatgaa ggcagagcta aaagtcagtt agaagaggga gatagagtca      180
ttataataaa accagatgga gcctttttaa ttcataaaga taaaaaaga gaacctgtaa      240 attggcaacc ttctggaagt agtataatat gggaagttga agataacttt tcatttttaa    300
aaagcattag aagaaagcca aagaagagt taaaggttgt tatttcagaa gtttatcatg      360
catgtgcttt taactgtgaa gattatgaag agataaatct aaggggtagt gaatcagaga    420
tggcagagat gattttttaga aatccagatt tgattgaaga aggatttaag cccatatcaa     480
gagagtatca gattcccact ggaatcgttg atattttagg aaaagataaa gagaataaat    540
gggttatctt agagctaaag agaaggagag ctgatttaca ggcagtttct caactaaaaa    600
ggtatgtgga atattttaaa aacaaatatg gtgaggataa agttagagga attttggttt    660
ctccctcttt aactactggg gcggaaaaat tgctgaaaga ggagaactta gaatttaaaa    720
gacttaatcc accaaaagga agtaaaagag atttaaaaca taacataaaa actaaaaaaa    780
caacagtttt agatgaatgg ctataaggat ccggctgcta ac                       822
```

```
<210> SEQ ID NO 15
<211> LENGTH: 28
<212> TYPE: DNA
<213> ORGANISM: Artificial Sequence
<220> FEATURE:
<223> OTHER INFORMATION: synthetic oligo nucleotide

<400> SEQUENCE: 15
gtgaactttc agccgccggg cagcaaag                                        28

<210> SEQ ID NO 16
<211> LENGTH: 28
<212> TYPE: DNA
<213> ORGANISM: Artificial Sequence
<220> FEATURE:
<223> OTHER INFORMATION: synthetic oligo nucleotide

<400> SEQUENCE: 16
cggctgaaag ttcaccggtt cgcgtttc                                        28

<210> SEQ ID NO 17
<211> LENGTH: 25
<212> TYPE: DNA
<213> ORGANISM: Artificial Sequence
<220> FEATURE:
<223> OTHER INFORMATION: synthetic oligo nucleotide

<400> SEQUENCE: 17
ctaaacttgg gtctcctcag ggttc                                           25

<210> SEQ ID NO 18
<211> LENGTH: 25
<212> TYPE: DNA
<213> ORGANISM: Artificial Sequence
<220> FEATURE:
<223> OTHER INFORMATION: synthetic oligo nucleotide

<400> SEQUENCE: 18
ctaaacttgg atctcctcag ggttc                                           25

<210> SEQ ID NO 19
<211> LENGTH: 25
<212> TYPE: DNA
<213> ORGANISM: Artificial Sequence
<220> FEATURE:
<223> OTHER INFORMATION: synthetic oligo nucleotide

<400> SEQUENCE: 19
ctaaacttgg ttctcctcag ggttc                                           25

<210> SEQ ID NO 20
<211> LENGTH: 25
<212> TYPE: DNA
<213> ORGANISM: Artificial Sequence
<220> FEATURE:
<223> OTHER INFORMATION: synthetic oligo nucleotide

<400> SEQUENCE: 20
ctaaacttgg ctctcctcag ggttc                                           25

<210> SEQ ID NO 21
<211> LENGTH: 25
<212> TYPE: DNA
<213> ORGANISM: Artificial Sequence
<220> FEATURE:
<223> OTHER INFORMATION: synthetic oligo nucleotide
```

```
<400> SEQUENCE: 21
gaaccctgag gagagccaag tttag                                              25

<210> SEQ ID NO 22
<211> LENGTH: 25
<212> TYPE: DNA
<213> ORGANISM: Artificial Sequence
<220> FEATURE:
<223> OTHER INFORMATION: synthetic oligo nucleotide

<400> SEQUENCE: 22
gaaccctgag gagaaccaag tttag                                              25

<210> SEQ ID NO 23
<211> LENGTH: 25
<212> TYPE: DNA
<213> ORGANISM: Artificial Sequence
<220> FEATURE:
<223> OTHER INFORMATION: synthetic oligo nucleotide

<400> SEQUENCE: 23
gaaccctgag gagatccaag tttag                                              25

<210> SEQ ID NO 24
<211> LENGTH: 25
<212> TYPE: DNA
<213> ORGANISM: Artificial Sequence
<220> FEATURE:
<223> OTHER INFORMATION: synthetic oligo nucleotide

<400> SEQUENCE: 24
gaaccctgag gagacccaag tttag                                              25

<210> SEQ ID NO 25
<211> LENGTH: 12
<212> TYPE: DNA
<213> ORGANISM: Artificial Sequence
<220> FEATURE:
<223> OTHER INFORMATION: synthetic oligo nucleotide

<400> SEQUENCE: 25
atgcctagcg ga                                                            12

<210> SEQ ID NO 26
<211> LENGTH: 12
<212> TYPE: DNA
<213> ORGANISM: Artificial Sequence
<220> FEATURE:
<223> OTHER INFORMATION: synthetic oligo nucleotide

<400> SEQUENCE: 26
atgcctatcg ga                                                            12

<210> SEQ ID NO 27
<211> LENGTH: 12
<212> TYPE: DNA
<213> ORGANISM: Artificial Sequence
<220> FEATURE:
<223> OTHER INFORMATION: synthetic oligo nucleotide

<400> SEQUENCE: 27
atgcctaacg ga                                                            12

<210> SEQ ID NO 28
```

```
<211> LENGTH: 12
<212> TYPE: DNA
<213> ORGANISM: Artificial Sequence
<220> FEATURE:
<223> OTHER INFORMATION: synthetic oligo nucleotide

<400> SEQUENCE: 28
atgcctaccg ga                                                         12

<210> SEQ ID NO 29
<211> LENGTH: 23
<212> TYPE: DNA
<213> ORGANISM: Artificial Sequence
<220> FEATURE:
<223> OTHER INFORMATION: synthetic oligo nucleotide

<400> SEQUENCE: 29
aatatccggt aggcattgaa gca                                             23

<210> SEQ ID NO 30
<211> LENGTH: 23
<212> TYPE: DNA
<213> ORGANISM: Artificial Sequence
<220> FEATURE:
<223> OTHER INFORMATION: synthetic oligo sequence

<400> SEQUENCE: 30
aatatccgtt aggcattgaa gca                                             23

<210> SEQ ID NO 31
<211> LENGTH: 25
<212> TYPE: DNA
<213> ORGANISM: Thermus thermophilus

<400> SEQUENCE: 31
gagccttccc tggtccttta cggcg                                           25

<210> SEQ ID NO 32
<211> LENGTH: 24
<212> TYPE: DNA
<213> ORGANISM: Thermus thermophilus

<400> SEQUENCE: 32
gttgcggagg aggtcgtcca ggag                                            24

<210> SEQ ID NO 33
<211> LENGTH: 25
<212> TYPE: DNA
<213> ORGANISM: Thermus thermophilus

<400> SEQUENCE: 33
gagcggaacc acgagaacac cctgg                                           25

<210> SEQ ID NO 34
<211> LENGTH: 24
<212> TYPE: DNA
<213> ORGANISM: Thermus thermophilus

<400> SEQUENCE: 34
ctccaggtcc gcctcttccc gctt                                            24

<210> SEQ ID NO 35
<211> LENGTH: 25
<212> TYPE: DNA
<213> ORGANISM: Thermus thermophilus
```

```
<400> SEQUENCE: 35
cggccctacc gctttagcct ggagg                                          25

<210> SEQ ID NO 36
<211> LENGTH: 24
<212> TYPE: DNA
<213> ORGANISM: Thermus thermophilus

<400> SEQUENCE: 36
ccacggcacc tccaagaagg cctc                                           24

<210> SEQ ID NO 37
<211> LENGTH: 25
<212> TYPE: DNA
<213> ORGANISM: Thermus thermophilus

<400> SEQUENCE: 37
gtagaggaag tggttcttcc cggcg                                          25

<210> SEQ ID NO 38
<211> LENGTH: 24
<212> TYPE: DNA
<213> ORGANISM: Thermus thermophilus

<400> SEQUENCE: 38
gaagctcccc ttcagggcct ccac                                           24

<210> SEQ ID NO 39
<211> LENGTH: 25
<212> TYPE: DNA
<213> ORGANISM: Homo sapiens

<400> SEQUENCE: 39
cctggtaggt tttctgggaa gggac                                          25

<210> SEQ ID NO 40
<211> LENGTH: 25
<212> TYPE: DNA
<213> ORGANISM: Homo sapiens

<400> SEQUENCE: 40
ctggtcctct gactgctctt ttcac                                          25

<210> SEQ ID NO 41
<211> LENGTH: 252
<212> TYPE: DNA
<213> ORGANISM: Homo sapiens

<400> SEQUENCE: 41
cctggtaggt tttctgggaa gggacagaag atgacagggg ccaggagggg gctggtgcag     60 ggccgccgg tgtaggagct gctggtgcag gggccacggg gggagcagcc tctggcattc    120
tgggagcttc atctggacct gggtcttcag tgaaccattg ttcaatatcg tccggggaca   180
gcatcaaatc atccattgct tgggacggca agggggactg tagatgggtg aaaagagcag   240
tcagaggacc ag                                                       252

<210> SEQ ID NO 42
<211> LENGTH: 26
<212> TYPE: DNA
<213> ORGANISM: Artificial Sequence
<220> FEATURE:
```

```
<223> OTHER INFORMATION: synthetic oligo nucleotide

<400> SEQUENCE: 42
gctggtgcag gggccacgag gggagc                                              26

<210> SEQ ID NO 43
<211> LENGTH: 26
<212> TYPE: DNA
<213> ORGANISM: Artificial Sequence
<220> FEATURE:
<223> OTHER INFORMATION: synthetic oligo nucleotide

<400> SEQUENCE: 43
ggccacgagg ggagcagcct ctggca                                              26

<210> SEQ ID NO 44
<211> LENGTH: 16
<212> TYPE: DNA
<213> ORGANISM: Artificial Sequence
<220> FEATURE:
<223> OTHER INFORMATION: synthetic oligo nucleotide

<400> SEQUENCE: 44
tgctccccgc gtggcc                                                         16

<210> SEQ ID NO 45
<211> LENGTH: 20
<212> TYPE: DNA
<213> ORGANISM: Artificial Sequence
<220> FEATURE:
<223> OTHER INFORMATION: synthetic oligo nucleotide

<400> SEQUENCE: 45
gcaatggatg atttgatgct                                                     20

<210> SEQ ID NO 46
<211> LENGTH: 20
<212> TYPE: DNA
<213> ORGANISM: Artificial Sequence
<220> FEATURE:
<223> OTHER INFORMATION: synthetic oligo nucleotide

<400> SEQUENCE: 46
aacgacggcc agtgaattag                                                     20
```

METHOD FOR USING HEAT-RESISTANT MISMATCH ENDONUCLEASE

TECHNICAL FIELD

The present invention relates to a heat-resistant mismatch endonuclease which recognizes and cleaves a mismatched base pair in a double-stranded nucleic acid, a composition comprising the mismatch endonuclease, and a method of using the mismatch endonuclease.

BACKGROUND ART

In recent years, biotechnology has been remarkably developed. Particularly, in consequence of large-scale genomic analyses accompanying advances in genomic analysis techniques, enormous information of genome sequences has been accumulated. In addition, based on combinations of the above-mentioned information with analyses of various physiological functions, many functional genetic mutations have been found. Analyses of these mutations have been used for genetic diagnoses of human beings as well as improvement of agricultural crops and isolation or creation of useful microorganisms, and thus have greatly contributed to general living.

The mutation analyses are performed by direct analyses of genomic sequences or by use of enzymes that recognize mismatched base pairs. A mutation analysis method comprises detection with a factor capable of binding specifically to a mismatched base pair formed from a mutant-type DNA and a wild-type DNA. A representative example of the mutation analysis method includes detection of mutation sites by use of MutS, MutT, and MutL complexes from *Escherichia coli* (Patent Literature 1).

A mutation analysis method comprising use of a mismatch endonuclease which specifically cleaves mismatch sites is also known. In the method, a mismatch endonuclease is used to cleave a DNA in the vicinity of a mismatched base pair, and the DNA fragments thus obtained are analyzed to detect the presence or absence and the position of mutations. As a representative example, a method comprising use of a Cell gene product from celery is known (Patent Literature 2), and the method is actually used for analyses of base mutations. However, the enzyme is not heat-resistant, and therefore cannot be used in techniques involving a high-temperature reaction process, such as PCR. Thus, in order to detect base mutations, the method requires four steps of amplification, formation of mismatches, cleavage of mismatches, and detection.

In addition to mutation analyses, examples of biotechnological techniques that have a lot of influence include nucleic acid amplification techniques.

A representative example of the nucleic acid amplification techniques is polymerase chain reaction (PCR) PCR is a technique for easily amplifying a desired fragment of a nucleic acid in vitro. PCR is an experimental technique which is essential in broad fields including the fields of biology, medicine, and agriculture, as well as research regarding genes. PCR is also applied to detection of mutated genes and analysis of methylation of DNA.

Isothermal nucleic acid amplification methods such as a LAMP method and an ICAN method do not require special equipment, and therefore they are used as cheaper methods for detection of nucleic acids.

For structural analyses of the whole genome which have been performed in recent years, a whole-genome amplification method is an important technique, in particular for analyses of scarce samples.

In these nucleic acid amplification methods, incorporation of incorrect bases occurs with a constant probability. The probability has been reduced through improvement of a polymerase or the like. However, the incorporation of incorrect bases still disturbs precise analyses.

The nucleic acid amplification techniques are used not only for amplification of a DNA having a specific nucleotide sequence but also for amplification of a mixture of DNAs having a common nucleotide sequence region at both ends. Specific examples of such nucleic acid amplification techniques include construction of genomic libraries or cDNA libraries. In constructing such libraries, however, a DNA molecule with a higher content is preferentially amplified, which may disturb analyses or screening of various kinds of DNAs.

To solve the above problem, the proportion of a DNA with a higher content is reduced by normalization utilizing self-hybridization (Non-patent Literature 1). SSH-PCR in which PCR and self-hybridization are combined is also used (Non-patent Literature 2). Using these methods, however, DNAs homologous to the DNA with a higher content may be also removed.

In detection of a DNA by a nucleic acid amplification method, a target DNA and a non-target DNA may compete for amplification. In other words, when a non-target DNA is amplified simultaneously with amplification of a target DNA, it is difficult to detect the target DNA. The above problem may be solved by use of real-time PCR in which probes such as cycling probes or TaqMan probes are used to detect only a target DNA. In the case where a non-target DNA exists in an excessively large amount relative to a target DNA, however, it is difficult to detect the target DNA because of false-positive reaction with many similar DNAs.

Such a problem may occur in detection of a small number of mutant alleles in the presence of normal alleles (for example, detection of circulating tumor genes), detection of a small number of methylated or non-methylated alleles by epigenetic assay, detection of a small amount of fetal DNA sequences circulating in the mother's blood, and the like.

To solve the above problem, a method termed restriction endonuclease-mediated selective polymerase chain reaction (REMS PCR) has been developed (Non-patent Literature 3). This method involves use of a heat-resistant restriction enzyme. In this method, a DNA having a mutant nucleotide sequence is selectively detected using primers which, for example, are designed so that cleavage by the restriction enzyme occurs only when a template has a normal nucleotide sequence. Depending on a target DNA to be detected, however, there may be no heat-resistant restriction enzyme having a recognition sequence suitable to detection by REMS PCR.

CITATION LIST

Patent Literature

Patent Literature 1: U.S. Pat. No. 5,922,539 B
Patent Literature 2: WO 01/062974

Non Patent Literature

Non-Patent Literature 1: "Nucleic Acids Research", 2004 February, vol. 32, No. 3, e37

Non-Patent Literature 2: "Methods in Molecular Biology", 2009, vol. 496, No. 2, pp. 223-243

Non-Patent Literature 3: "American Society for Investigative Pathology", 1998 August, vol. 153, No. 2, pp. 373-379

SUMMARY OF INVENTION

Technical Problems

Objectives of the present invention include provision of a heat-resistant mismatch endonuclease, a composition comprising the mismatch endonuclease, and a method of using the mismatch endonuclease.

Solution to Problems

As a result of intensive efforts under the above circumstances, the present inventors have found that a protein from archaebacteria, which has been regarded as a factor in the replication mechanism, has a heat-resistant mismatch endonuclease activity.

The present inventors also have found that in a nucleic acid amplification reaction in the presence of the mismatch endonuclease and an oligodeoxynucleotide which is designed to generate one or more mismatches when the oligodeoxynucleotide is hybridized with a nucleic acid having a specific nucleotide sequence, amplification of the DNA having the specific nucleotide sequence is inhibited.

Furthermore, the present inventors have successfully created a mutant of the heat-resistant mismatch endonuclease which has increased specificity. It has been found that when the mutant mismatch endonuclease is used, cleavage of base pairs other than a specific mismatched base pair is inhibited, allowing more specific inhibition of amplification. Thus the present invention has been completed.

Specifically, the first aspect of the present invention provides:

A method of cleaving a double-stranded nucleic acid, the method comprising:
  treating a double-stranded nucleic acid having a mismatched base pair with at least one polypeptide selected from the group consisting of the following (i) to (iii) to cleave both strands of the double-stranded nucleic acid at the position of the mismatched base pair,
  (i) a polypeptide having an amino acid sequence of SEQ ID NO:1;
  (ii) a polypeptide having an amino acid sequence which differs from the amino acid sequence of SEQ ID NO:1 by substitution, deletion, insertion and/or addition of 1 to 10 amino acid residues, and having a mismatch endonuclease activity; and
  (iii) a polypeptide having an amino acid sequence which shares at least 50% amino acid sequence identity with the amino acid sequence of SEQ ID NO:1, and having a mismatch endonuclease activity;

The method of cleaving a double-stranded nucleic acid, wherein the mismatched base pair comprises contiguous 1 to 8 mismatched base pairs existing between two base pairs which are normally paired on the double-stranded nucleic acid;

A composition comprising the following (a) to (c):
  (a) a DNA polymerase;
  (b) at least one pair of oligonucleotide primers; and
  (c) at least one polypeptide selected from the group consisting of the following (i) to (iii):
    (i) a polypeptide having an amino acid sequence of SEQ ID NO:1;
    (ii) a polypeptide having an amino acid sequence which differs from the amino acid sequence of SEQ ID NO:1 by substitution, deletion, insertion and/or addition of 1 to 10 amino acid residues, and having a mismatch endonuclease activity; and
    (iii) a polypeptide having an amino acid sequence which shares at least 50% amino acid sequence identity with the amino acid sequence of SEQ ID NO:1, and having a mismatch endonuclease activity;

A method of amplifying a nucleic acid, the method comprising the following steps (a) and (b):
  (a) preparing a composition comprising the composition according to claim 3 and a nucleic acid molecule as a template; and
  (b) reacting the composition obtained by step (a) under suitable conditions to perform nucleic acid amplification;

The method of amplifying a nucleic acid, wherein the nucleic amplification is performed by a polymerase chain reaction (PCR) method, an isothermal nucleic acid amplification method, or a multiple displacement amplification (MDA) method; A polypeptide selected from the group consisting of the following (A) to (C):
  (A) a polypeptide having an amino acid sequence which differs from an amino acid sequence of SEQ ID NO:1 by substitution of tryptophan at position 77 with another amino acid residue, and having a mismatch endonuclease activity;
  (B) a polypeptide having an amino acid sequence which differs from the amino acid sequence of the polypeptide of (A) by substitution, deletion, insertion and/or addition of 1 to 10 amino acid residues other than the amino acid residue at position 77, and having a mismatch endonuclease activity; and
  (C) a polypeptide having an amino acid sequence which shares at least 50% amino acid sequence identity with the amino acid sequence of SEQ ID NO:1, in which an amino acid residue corresponding to tryptophan at position 77 in the amino acid sequence of SEQ ID NO:1 is substituted with another amino acid residue, and having a mismatch endonuclease activity;

The polypeptide may be selected from the group consisting of the following (A) to (C):
  (A) a polypeptide having an amino acid sequence of SEQ ID NO:2;
  (B) a polypeptide having an amino acid sequence which differs from the amino acid sequence of SEQ ID NO:2 by substitution, deletion, insertion and/or addition of 1 to 10 amino acid residues other than phenylalanine at position 77, and having a mismatch endonuclease activity; and
  (C) a polypeptide having an amino acid sequence which shares at least 50% amino acid sequence identity with the amino acid sequence of SEQ ID NO:1, in which an amino acid residue corresponding to tryptophan at position 77 in the amino acid sequence of SEQ ID NO:1 is substituted with phenylalanine, and having a mismatch endonuclease activity;

A method of inhibiting amplification of a nucleic acid having a specific nucleotide sequence in a nucleic acid amplification reaction, the method comprising a step of performing the nucleic acid amplification reaction in the presence of the following (a) to (d):
  (a) an oligodeoxynucleotide which is designed to generate one to several mismatches when the oligodeoxynucleotide is hybridized with the nucleic acid having a specific nucleotide sequence or a complementary strand thereof;
(b) a DNA polymerase;
(c) at least one pair of oligonucleotide primers; and
(d) a polypeptide having a mismatch endonuclease activity;

The method of inhibiting amplification of a nucleic acid having a specific nucleotide sequence in a nucleic acid amplification reaction, wherein the nucleic acid amplification reaction is a polymerase chain reaction (PCR) method or an isothermal nucleic acid amplification method;

The method of inhibiting amplification of a nucleic acid having a specific nucleotide sequence in a nucleic acid amplification reaction, wherein the polypeptide having a mismatch endonuclease activity is at least one polypeptide selected from the group consisting of the following (i) to (vi):
(i) a polypeptide having an amino acid sequence of SEQ ID NO:1;
(ii) a polypeptide having an amino acid sequence which differs from the amino acid sequence of SEQ ID NO:1 by substitution, deletion, insertion and/or addition of 1 to 10 amino acid residues, and having a mismatch endonuclease activity;
(iii) a polypeptide having an amino acid sequence which shares at least 50% amino acid sequence identity with the amino acid sequence of SEQ ID NO:1, and having a mismatch endonuclease activity;
(iv) a polypeptide having an amino acid sequence of SEQ ID NO:2;
(v) a polypeptide having an amino acid sequence which differs from the amino acid sequence of SEQ ID NO:2 by substitution, deletion, insertion and/or addition of 1 to 10 amino acid residues other than phenylalanine at position 77, and having a mismatch endonuclease activity; and
(vi) a polypeptide having an amino acid sequence which shares at least 50% amino acid sequence identity with the amino acid sequence of SEQ ID NO:1, in which an amino acid residue corresponding to tryptophan at position 77 in the amino acid sequence of SEQ ID NO:1 is substituted with phenylalanine, and having a mismatch endonuclease activity;

A method of preferentially amplifying a target DNA, the method comprising inhibiting amplification of a DNA having a nucleotide sequence different from that of the target DNA in one to several nucleotides by the method of inhibiting amplification of a nucleic acid having a specific nucleotide sequence in a nucleic acid amplification reaction:

The method of preferentially amplifying a target DNA, which is used for amplifying a DNA having a wild-type nucleotide sequence or the DNA containing a single nucleotide polymorphism mutation, wherein the amplification of the wild-type DNA and the amplification of the DNA containing a single nucleotide polymorphism mutation are distinguished from each other; The method of preferentially amplifying a target DNA, wherein the single nucleotide polymorphism mutation correlates with canceration, or a therapeutic effect of an agent for the treatment of a cancer; and The method of preferentially amplifying a target DNA, wherein the DNA amplification reaction is performed by a polymerase chain reaction (PCR) method or an isothermal nucleic acid amplification method.

Effects of the Invention

According to the present invention, a heat-resistant mismatch endonuclease which has great utility in biotechnology, a composition comprising the mismatch endonuclease, and a method of using the mismatch endonuclease are provided.

BRIEF DESCRIPTION OF DRAWINGS

FIG. 1 shows results of polyacrylamide gel electrophoresis in Example 2.
FIG. 2 shows mismatch cleavage activities of protein PF0012 on the basis of increases of fluorescent intensity in Example 2.
FIG. 3 shows mismatch cleavage activities of PF0012 homologous protein on the basis of increases of fluorescent intensity in Example 3.
FIG. 4 shows mismatch cleavage activities of mutant PF0012 homologous protein on the basis of increases of fluorescent intensity in Example 5.
FIG. 5 shows inhibition of amplification of a DNA having a specific nucleotide sequence by real-time PCR technique in Example 6.
FIG. 6 shows detection of a single nucleotide-mutated gene by an HRM analysis method.

DESCRIPTION OF EMBODIMENTS

In the present invention, the word "mismatch" refers to base pairings different from Watson-Crick base pairs present in double-stranded nucleic acids, in other words, binding of bases in combinations other than base pairings of G (guanine base)-C (cytosine base), and A (adenine base)-T (thymine base) or U (uracil base).

As used herein, a polypeptide having a mismatch endonuclease activity (sometimes, referred to as a mismatch endonuclease) means a nuclease having the activity of cleaving mismatch sites present in double-stranded nucleic acids. The mismatch endonuclease activity includes an activity of cleaving phosphodiester bonds adjacent to nucleotides forming mismatched base pairs, and an activity of cleaving phosphodiester bonds adjacent to nucleotides located 1 to 5, preferably 1 to 3 base pairs away from mismatched base pairs. In the present invention, the mismatch endonuclease may be a nuclease having the activity of specifically recognizing a specific mismatched base pair in a double-stranded nucleic acid to cleave the double-stranded nucleic acid (for example, a nuclease which specifically recognizes GT mismatches, or a nuclease which specifically recognizes GT mismatches and GG mismatches). In the present invention, the heat-resistant mismatch endonuclease may have, in addition to the activity of cleaving mismatch sites present in double-stranded nucleic acids, the activity of recognizing single-stranded DNAs, junction parts between single-stranded nucleic acids and double-stranded nucleic acids, double flap structure, replication fork structure, D-loop structure, and/or Holiday junction structure with a nick to cleave the nucleic acids. As used herein, the heat-resistant mismatch endonuclease means a nuclease that exhibits the activity of cleaving mismatch sites in double-stranded nucleic acids at temperature of 50° C. or higher. In the present invention, a heat-resistant mismatch endonuclease is preferably used.

Examples of the heat-resistant mismatch endonuclease used in the present invention include, but not limited to, polypeptides having a heat-resistant mismatch endonuclease activity from archaebacteria. The present inventors have found that polypeptide PF0012 (RefSeq ID: NP 577741, SEQ ID NO:1) from *Pyrococcus furiosus*, which has been to date regarded as a factor in the replication mechanism, is a heat-resistant mismatch endonuclease. Furthermore, the present inventors have found that polypeptide MJ_0225 (RefSeq ID: NP_247194, SEQ ID NO:8) from *Methanocaldococcus jannaschii* and polypeptide TERMP_01877 (RefSeq ID: YP_004072075, SEQ ID NO:7) from *Thermococcus barophilus*, which are homologs of PF0012, are also heat-resistant mismatch endonucleases. MJ_0225 and TERMP_01877 have 57% and 73% sequence identity with SEQ ID NO:1 respectively. Preferred examples of the heat-resistant mismatch endonucleases used in the present invention include a polypeptide having an amino acid sequence of SEQ ID NO:1; a polypeptide having an amino acid sequence which differs from the amino acid sequence of SEQ ID NO:1 by substitution, deletion, insertion and/or addition of 1 to 10 amino acid residues, for example 1, 2, 3, 4, 5, 6, 7, 8, 9, or 10 amino acid residues; and a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:1. Preferred examples of the heat-resistant mismatch endonucleases used in the present invention also include a polypeptide having an amino acid sequence of SEQ ID NO:7; a polypeptide having an amino acid sequence which differs from the amino acid sequence of SEQ ID NO:7 by substitution, deletion, insertion and/or addition of 1 to 10 amino acid residues, for example 1, 2, 3, 4, 5, 6, 7, 8, 9, or 10 amino acid residues; and a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:7. Preferred examples of the heat-resistant mismatch endonucleases used in the present invention also include a polypeptide having an amino acid sequence of SEQ ID NO:8; a polypeptide having an amino acid sequence which differs from the amino acid sequence of SEQ ID NO:8 by substitution, deletion, insertion and/or addition of 1 to 10 amino acid residues, for example 1, 2, 3, 4, 5, 6, 7, 8, 9, or 10 amino acid residues; and a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:8.

Furthermore, the present inventors have found that a polypeptide having an amino acid sequence which differs from the amino acid sequence of SEQ ID NO:1 by substitution of tryptophan at position 77 with another amino acid residue, preferably phenylalanine is a heat-resistant mismatch endonuclease that specifically recognizes mismatch G (guanine base)-G (guanine base). As a result of measurement, the cleavage activity of the mismatch endonuclease on the mismatched base pair formed from guanine bases was 10 times or more the cleavage activity on other mismatched base pairs. Thus, an aspect of the present invention includes a polypeptide having an amino acid sequence of SEQ ID NO:2 thus created and homologs thereof. Examples of the polypeptide having an amino acid sequence of SEQ ID NO:2 and homologs thereof include a polypeptide having an amino acid sequence which differs from the amino acid sequence of SEQ ID NO:1 by substitution of tryptophan at position 77 with another amino acid residue, and having a mismatch endonuclease activity; a polypeptide having an amino acid sequence which differs from the amino acid sequence of the above-mentioned polypeptide by substitution, deletion, insertion and/or addition of 1 to 10 amino acid residues, for example 1, 2, 3, 4, 5, 6, 7, 8, 9, or 10 amino acid residues other than the amino acid residue at position 77, and having a mismatch endonuclease activity; and a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:1, in which an amino acid residue corresponding to tryptophan at position 77 in the amino acid sequence of SEQ ID NO:1 is an amino acid residue other than tryptophan, and having a mismatch endonuclease activity. Such mismatch endonucleases are suitable for various uses as mentioned later, for example, a method comprising removing a DNA containing a specific DNA sequence and amplifying and detecting other DNAs.

The mismatch endonuclease activity may be measured by use of a double-stranded nucleic acid containing a mismatched base pair as a substrate. Specifically, after a double-stranded nucleic acid containing a mismatched base pair is prepared, the double-stranded nucleic acid is reacted with a mismatch endonuclease in which the amount of double-stranded nucleic acid is excess relative to the amount of the mismatch endonuclease, and then, the amount of nucleic acids cleaved per unit time is measured. The cleaved double-stranded nucleic acids can be quantified separately from non-cleaved nucleic acids, for example, by electrophoresis. A double-stranded nucleic acid double labeled with a fluorescent substance and a quencher substance may be used so that an increase in fluorescent intensity can be detected only when the double-stranded nucleic acid is cleaved. Using such a double-stranded nucleic acid double labeled with a fluorescent substance and a quencher substance, the mismatch endonuclease activity can be easily determined by measuring the fluorescent intensity in a reaction mixture at suitable time intervals. The cleavage activity on a specific mismatched base pair can be determined by changing the bases forming a mismatched base pair present in a double-stranded nucleic acid used as a substrate.

The method of cleaving a double-stranded nucleic acid of the present invention comprises treating a double-stranded nucleic acid having a mismatched base pair with a polypeptide having the amino acid sequence of SEQ ID NO:1 or a homolog thereof. Examples of the homolog of the polypeptide having the amino acid sequence of SEQ ID NO:1 include, but not limited to, a polypeptide having an amino acid sequence which differs from the amino acid sequence of SEQ ID NO:1 by substitution, deletion, insertion and/or addition of 1 to 10 amino acid residues, for example 1, 2, 3, 4, 5, 6, 7, 8, 9, or 10 amino acid residues, and having a mismatch endonuclease activity; a polypeptide having an amino acid sequence which shares at least 50% amino acid sequence identity, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:1, and having a mismatch endonuclease activity; and a polypeptide having the amino acid sequence of SEQ ID NO:2 and a homolog thereof. Examples of organisms from which the polypeptide used in the double-stranded nucleic acid cleavage method of the present invention is derived include archaebacteria, preferably heat-resistant archaebacteria, more preferably *Pyrococcus furiosus*, *Thermococcus barophilus*, and *Methanocaldococcus jannaschii*. In the double-stranded nucleic acid cleavage method of the present invention, polypeptide MJ_0225 (RefSeq ID: NP_247194, SEQ ID NO:8) from *Methanocaldococcus jannaschii*, which is a homolog of PF0012, or a homolog of MJ_0225, or polypeptide TERMP_01877 (RefSeq ID: YP_004072075, SEQ ID NO:7) from *Thermococcus barophilus*, which is a homolog of PF0012, or a homolog of TERMP_01877 may be also used. Examples of the homolog of the polypeptide having the amino acid sequence of SEQ ID NO:7 include, but not limited to, a polypeptide having an amino acid sequence which differs from the amino acid sequence of SEQ ID NO:7 by substitution, deletion, insertion and/or addition of 1 to 10 amino acid residues, for example 1, 2, 3, 4, 5, 6, 7, 8, 9, or 10 amino acid residues, and having a mismatch endonuclease activity; and a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:7, and having a mismatch endonuclease activity. Examples of the homolog of the polypeptide having the amino acid sequence of SEQ ID NO:8 include, but not limited to, a polypeptide having an amino acid sequence which differs from the amino acid sequence of SEQ ID NO:8 by substitution, deletion, insertion and/or addition of 1 to 10 amino acid residues, for example 1, 2, 3, 4, 5, 6, 7, 8, 9, or 10 amino acid residues, and having a mismatch endonuclease activity; and a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:8, and having a mismatch endonuclease activity.

The mismatched base pair in the double-stranded nucleic acid cleavage method of the present invention is present within the double-stranded nucleic acid (between two base pairs normally base-pairing). The mismatched base pairs are not limited to one mismatched base pair present within the double-stranded nucleic acid. The mismatched base pairs also include plural mismatched base pairs present at intervals within the double-stranded nucleic acid, and two or more contiguous mismatched base pairs present within the double-stranded nucleic acid. Examples of the mismatched base pairs in the double-stranded nucleic acid cleavage method of the present invention include preferably 1 to 8 contiguous mismatched base pairs present within the double-stranded nucleic acid, more preferably 1 to 4 contiguous mismatched base pairs present within the double-stranded nucleic acid, and still more preferably 2 contiguous mismatched base pairs or one mismatched base pair present within the double-stranded nucleic acid. In the double-stranded nucleic acid cleavage method of the present invention, when plural mismatched base pairs are present within the double-stranded nucleic acid, the plural mismatched base pairs may be mismatched base pairs of the same kind or different kinds.

Examples of the double-stranded nucleic acid having a mismatched base pair include a nucleic acid from a organism sample, for example, a PCR product, a genomic DNA, or a fragment thereof, and a synthetic nucleic acid. The double-stranded nucleic acid having a mismatched base pair may also be a nucleic acid mixture obtained by melting and reannealing of a mixture of plural organism samples, or a mixture of nucleic acids from an organism sample and a synthetic nucleic acid. For example, when a nucleic acid containing a mutation and a wild-type nucleic acid are mixed, melted, and reannealed, a mismatched base pair is formed and cleavage by a mismatch endonuclease occurs at the position of the mismatched base pair. After cleavage by a mismatch endonuclease, the size of the nucleic acid fragment thus cleaved is observed to determine the presence or absence and the position of a mutation. Use of the mismatch endonuclease of the present invention allows mutation analysis by one-step reaction in which the mismatch endonuclease is simply added to a reaction mixture for a nucleic acid amplification method such as PCR. It is known that when the number of cycles in PCR is increased to exceed a certain number, no effect in the amplification is obtained. The main causes are depletion of the nucleic acid added to the reaction mixture, or competition between primers and reaction products for annealing. At that time, annealing between the reaction products occurs. If a template containing a mutation and a wild-type template coexist, the reaction products amplified from these are annealed each other to generate a mismatched base pair at the mutation site. Thus, mutation analysis can be done simply by performing PCR in the presence of the mismatch endonuclease of the present invention through more cycles than usual. Specifically, the present invention provides a mutation analysis method comprising treatment of a double-stranded nucleic acid with a polypeptide having the amino acid sequence of SEQ ID NO:1 or a homolog thereof. The present invention further provides a mutation analysis method comprising treatment of a double-stranded nucleic acid with a polypeptide having the amino acid sequence of SEQ ID NO:7 or a homolog thereof. The present invention further provides a mutation analysis method comprising treatment of a double-stranded nucleic acid with a polypeptide having the amino acid sequence of SEQ ID NO:8 or a homolog thereof.

In the process of nucleic acid amplification reaction, the double-stranded nucleic acid cleavage method of the present invention can be performed. By addition of a mismatch endonuclease to a reaction mixture for nucleic acid amplification, a double-stranded nucleic acid having a mismatched base pair generated by incorporation of an incorrect base during the amplification process is cleaved.

As a result, amplification of a nucleic acid having a different sequence from that of a template nucleic acid before the reaction initiation is inhibited. Thus, nucleic acid amplification with a decreased error rate is attained. Specifically, the present invention provides a nucleic acid amplification method comprising a step of cleaving a double-stranded nucleic acid having a mismatched base pair by using a polypeptide having the amino acid sequence of SEQ ID NO:1 or a homolog thereof. The present invention further provides a nucleic acid amplification method comprising a step of cleaving a double-stranded nucleic acid having a mismatched base pair by using a polypeptide having the amino acid sequence of SEQ ID NO:7 or a homolog thereof. The present invention further provides a nucleic acid amplification method comprising a step of cleaving a double-stranded nucleic acid having a mismatched base pair by using a polypeptide having the amino acid sequence of SEQ ID NO:8 or a homolog thereof. The step of cleaving a double-stranded nucleic acid having a mismatched base pair may be performed simultaneously with a step of nucleic acid amplification. An aspect of the present invention also includes a composition comprising (a) a DNA polymerase; (b) at least one pair of oligonucleotide primers; and (c) at least one polypeptide selected from the group consisting of (i) a polypeptide having an amino acid sequence of SEQ ID NO:1; (ii) a polypeptide having an amino acid sequence which differs from the amino acid sequence of SEQ ID NO:1 by substitution, deletion, insertion and/or addition of 1 to 10 amino acid residues, for example 1, 2, 3, 4, 5, 6, 7, 8, 9, or 10 amino acid residues, and having a mismatch endonuclease activity; and (iii) a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:1, and having a mismatch endonuclease activity. As another aspect of the present invention, a composition is provided, comprising (a) a DNA polymerase; (b) at least one pair of oligonucleotide primers; and (c) at least one polypeptide selected from the group consisting of (i) a polypeptide having an amino acid sequence of SEQ ID NO:7; (ii) a polypeptide having an amino acid sequence which differs from the amino acid sequence of SEQ ID NO:7 by substitution, deletion, insertion and/or addition of 1 to 10 amino acid residues, for example 1, 2, 3, 4, 5, 6, 7, 8, 9, or 10 amino acid residues, and having a mismatch endonuclease activity; and (iii) a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:7, and having a mismatch endonuclease activity. As another aspect of the present invention, a composition is also provided, comprising (a) a DNA polymerase; (b) at least one pair of oligonucleotide primers; and (c) at least one polypeptide selected from the group consisting of (i) a polypeptide having an amino acid sequence of SEQ ID NO:8; (ii) a polypeptide having an amino acid sequence which differs from the amino acid sequence of SEQ ID NO:8 by substitution, deletion, insertion and/or addition of 1 to 10 amino acid residues, for example 1, 2, 3, 4, 5, 6, 7, 8, 9, or 10 amino acid residues, and having a mismatch endonuclease activity; and (iii) a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:8, and having a mismatch endonuclease activity.

An aspect of the present invention also includes a nucleic acid amplification method comprising a step of preparing a composition comprising the composition for nucleic acid amplification as mentioned above and a nucleic acid molecule as a template, and a step of reacting the composition thus obtained under suitable conditions to perform nucleic acid amplification.

The above-mentioned composition may further contain at least one selected from the group consisting of a reaction buffer, a divalent metal ion, a deoxyribonucleotide, an oligonucleotide probe, and an intercalating dye. When the above-mentioned composition is used in nucleic acid amplification reaction, the composition may further contain a nucleic acid as a template for the nucleic acid amplification reaction. The reaction buffer means a compound or mixture having the activity of decreasing variation of hydrogen-ion concentration (pH). A mixed solution of weak acid and a salt thereof or weak base and a salt thereof is broadly used as the reaction buffer for the purpose of pH control, because the mixed solution has strong buffering action. Examples of the reaction buffer used in the present invention include Good's buffers such as Tris-HCl, and HEPES-KOH, and phosphate buffers such as a sodium phosphate buffer. Examples of the divalent metal ion include a magnesium ion, a manganese ion, a zinc ion, and a cobalt ion. The divalent metal ion may be provided as a salt form such as a chloride, a sulfate, or an acetate.

Examples of a method for the nucleic acid amplification include, but not limited to, a method of amplifying a DNA. Examples of the method of amplifying a DNA include a polymerase chain reaction (PCR) method, a multiple displacement amplification (MDA) method, and an isothermal nucleic acid amplification method such as an ICAN method and a LAMP method.

The concentration of a polypeptide having a mismatch endonuclease activity in the above-mentioned composition for nucleic acid amplification reaction may be determined by determining a concentration that does not inhibit a DNA amplification reaction or a concentration effective for cleavage of a mismatched based pair in each reaction system as appropriate.

As the at least one pair of primers contained in the above-mentioned composition for nucleic acid amplification reaction, two or more primers suitable for each nucleic acid amplification method are selected. These primers may be DNA primers, RNA primers, or chimeric primers in which a part of a DNA molecule is replaced by RNA, as long as the desired amplification is attained. The primers may also be primers containing a known nucleic acid analog, and labeled primers, for example, with a fluorescent dye for the purpose of detection.

The present inventors have further found that amplification of a nucleic acid having a specific nucleotide sequence in a nucleic acid amplification reaction can be inhibited by use of a mismatch endonuclease and a suitably designed oligodeoxynucleotide. Thus an aspect of the present invention also includes a method of inhibiting amplification of a nucleic acid having a specific nucleotide sequence in a nucleic acid amplification reaction, comprising a step of performing the nucleic acid amplification reaction in the presence of (a) an oligodeoxynucleotide which is designed to generate one to several mismatches when the oligodeoxynucleotide is hybridized with the nucleic acid having a specific nucleotide sequence, (b) a DNA polymerase, (c) at least one pair of oligonucleotide primers, and (d) a polypeptide having a mismatch endonuclease activity. An aspect of the present invention also includes a method of preferentially amplifying a target DNA, comprising inhibiting amplification of a DNA having a specific nucleotide sequence different from the nucleotide sequence of the target DNA in one to several nucleotides by use of the above-mentioned method of inhibiting amplification of a nucleic acid having a specific nucleotide sequence in a nucleic acid amplification reaction.

The oligodeoxynucleotide in the above (a) is not particularly limited, as long as it is an oligodeoxynucleotide designed to generate one to several mismatches when it is hybridized with a nucleic acid having a specific nucleotide sequence. The oligodeoxynucleotide may be a so-called chimeric oligodeoxynucleotide in which a part of a DNA molecule is replaced by RNA. The 3' end of the oligodeoxynucleotide may be modified so as to inhibit an extension reaction from the oligodeoxynucleotide by a DNA polymerase, to which the present invention is not particularly limited. Examples of the modification include amination. The oligodeoxynucleotide may be protected from cleavage with a deoxyribonuclease by phosphorothioation or other modifications, as long as the nucleic acid to which the oligodeoxynucleotide is bound undergoes cleavage with the polypeptide having a mismatch endonuclease activity. The oligodeoxynucleotide may be labeled with a fluorescent dye or a quencher for the purpose of detection.

The length of the oligodeoxynucleotide may be appropriately determined so that the oligodeoxynucleotide can be hybridized with the nucleic acid having a specific nucleotide sequence under conditions of the reaction performed. The position of a mismatch generated when the oligodeoxynucleotide is hybridized with the nucleic acid having a specific nucleotide sequence is preferably at least 3 nucleotides away from the 5' end and 3' end of the oligodeoxynucleotide.

For the method of inhibiting amplification of a nucleic acid having a specific nucleotide sequence in a nucleic acid amplification reaction of the present invention, any mismatch endonuclease having the activity of specifically cleaving a mismatch site can be used. For example, when a heat-resistant DNA polymerase is used in a nucleic acid amplification method including a reaction at a high temperature such as a PCR method, a heat-resistant mismatch endonuclease is preferably used. In such a case, preferably used is the heat-resistant mismatch endonuclease, that is, at least one polypeptide selected from the group consisting of (i) a polypeptide having an amino acid sequence of SEQ ID NO:1; (ii) a polypeptide having an amino acid sequence which differs from the amino acid sequence of SEQ ID NO:1 by substitution, deletion, insertion and/or addition of 1 to 10 amino acid residues, for example 1, 2, 3, 4, 5, 6, 7, 8, 9, or 10 amino acid residues, and having a mismatch endonuclease activity; and (iii) a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:1, and having a mismatch endonuclease activity; (iv) a polypeptide having an amino acid sequence of SEQ ID NO:7; (v) a polypeptide having an amino acid sequence which differs from the amino acid sequence of SEQ ID NO:7 by substitution, deletion, insertion and/or addition of 1 to 10 amino acid residues, for example 1, 2, 3, 4, 5, 6, 7, 8, 9, or 10 amino acid residues, and having a mismatch endonuclease activity; and (vi) a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:7, and having a mismatch endonuclease activity; (vii) a polypeptide having an amino acid sequence of SEQ ID NO:8; (viii) a polypeptide having an amino acid sequence which differs from the amino acid sequence of SEQ ID NO:8 by substitution, deletion, insertion and/or addition of 1 to 10 amino acid residues, for example 1, 2, 3, 4, 5, 6, 7, 8, 9, or 10 amino acid residues, and having a mismatch endonuclease activity; and (ix) a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:8, and having a mismatch endonuclease activity, but to which the present invention is not particularly limited.

For the method of inhibiting amplification of a nucleic acid having a specific nucleotide sequence in a nucleic acid amplification reaction of the present invention, a mismatch endonuclease having the activity of specifically cleaving only a double-stranded nucleic acid containing a specific mismatched base pair is preferably used. In such a case, the nucleotide sequence whose amplification is inhibited can be limited to one kind of nucleotide sequence. For example, a polypeptide having the amino acid sequence of SEQ ID NO:2 which differs from the amino acid sequence of SEQ ID NO:1 by substitution of tryptophan at position 77 with another amino acid residue specifically cleaves a double-stranded nucleic acid containing a G (guanine base)-G (guanine base) mismatch. Thus, when the polypeptide having the amino acid sequence of SEQ ID NO:2 is used, a double-stranded nucleic acid in which a base other than G (guanine base) is present at the mismatch site is not cleaved and does not undergo inhibition of amplification. Specifically, a polypeptide having an amino acid sequence which differs from the amino acid sequence of SEQ ID NO:1 by substitution of tryptophan at position 77 with another amino acid residue, and a homolog thereof are preferably used for the method of inhibiting amplification of a nucleic acid having a specific nucleotide sequence.

Therefore, the present invention further provides a composition for nucleic acid amplification reaction, comprising the following (a) to (d):

(a) an oligodeoxynucleotide which is designed to generate one to several mismatches when the oligodeoxynucleotide is hybridized with a nucleic acid having a specific nucleotide sequence or a complementary strand thereof;

(b) a DNA polymerase;

(c) at least one pair of oligonucleotide primers; and (d) at least one polypeptide selected from the group consisting of the following (i) to (xii):

(i) a polypeptide having an amino acid sequence of SEQ ID NO:1;

(ii) a polypeptide having an amino acid sequence which differs from the amino acid sequence of SEQ ID NO:1 by substitution, deletion, insertion and/or addition of 1 to 10 amino acid residues, for example 1, 2, 3, 4, 5, 6, 7, 8, 9, or 10 amino acid residues, and having a mismatch endonuclease activity;

(iii) a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:1, and having a mismatch endonuclease activity;

(iv) a polypeptide having an amino acid sequence of SEQ ID NO:2;

(v) a polypeptide having an amino acid sequence which differs from the amino acid sequence of SEQ ID NO:2 by substitution, deletion, insertion and/or addition of 1 to 10 amino acid residues, for example 1, 2, 3, 4, 5, 6, 7, 8, 9, or 10 amino acid residues other than phenylalanine at position 77, and having a mismatch endonuclease activity;

(vi) a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:1, in which an amino acid residue corresponding to tryptophan at position 77 in the amino acid sequence of SEQ ID NO:1 is substituted with another amino acid residue, and having a mismatch endonuclease activity;

(vii) a polypeptide having an amino acid sequence of SEQ ID NO:7;

(viii) a polypeptide having an amino acid sequence which differs from the amino acid sequence of SEQ ID NO:7 by substitution, deletion, insertion and/or addition of 1 to 10 amino acid residues, for example 1, 2, 3, 4, 5, 6, 7, 8, 9, or 10 amino acid residues, and having a mismatch endonuclease activity;

(ix) a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:7, and having a mismatch endonuclease activity;

(x) a polypeptide having an amino acid sequence of SEQ ID NO:8;

(xi) a polypeptide having an amino acid sequence which differs from the amino acid sequence of SEQ ID NO:8 by substitution, deletion, insertion and/or addition of 1 to 10 amino acid residues, for example 1, 2, 3, 4, 5, 6, 7, 8, 9, or 10 amino acid residues, and having a mismatch endonuclease activity; and (xii) a polypeptide having an amino acid sequence which shares at least 50%, at least 55%, at least 60%, at least 65%, at least 70%, or at least 75% amino acid sequence identity, preferably at least 80% amino acid sequence identity, more preferably at least 85% amino acid sequence identity, still more preferably at least 90% amino acid sequence identity, most preferably at least 95% amino acid sequence identity with the amino acid sequence of SEQ ID NO:8, and having a mismatch endonuclease activity. The above-mentioned composition may further contain at least one selected from the group consisting of a reaction buffer, a divalent metal ion, a deoxyribonucleotide, an oligonucleotide probe, and an intercalating dye. The above-mentioned composition may further contain a nucleic acid as a template for nucleic amplification reaction.

The method of inhibiting amplification of a nucleic acid having a specific nucleotide sequence in a nucleic acid amplification reaction of the present invention can be performed by any nucleic acid amplification methods. A method of amplifying a DNA is preferably used, but which the present invention is limited to. The present invention can be performed, for example, by a PCR method, an MDA method, or an isothermal nucleic acid amplification method such as a LAMP method or an ICAN method.

The method of inhibiting amplification of a nucleic acid having a specific nucleotide sequence in a nucleic acid amplification reaction of the present invention can be applied to amplification of any nucleic acids. When a DNA is used as a target to be amplified, examples of the DNA include a DNA present in an artificially prepared DNA mixture, a sample from environment, an organism sample, or a DNA mixture prepared from the above-mentioned sample. Examples of the organism sample include, but not limited to, samples from mammals such as human. Examples of the DNA mixture include, but not limited to, a mixture of genomic DNA fragments, a mixture of cDNAs generated from mRNAs by reverse transcription reaction, and a mixture of plural PCR products. Examples of the DNA having a specific nucleotide sequence which is subjected to inhibition of amplification include a reverse transcription product from a rRNA which is not separated and remains, and a low-molecular DNA which is generated by pairing between primers. When a gene library followed by functional screening is amplified, a library capable of efficiently searching an unknown gene can be made by inhibiting amplification of a DNA having a sequence of a known gene exhibiting a positive signal.

The concentration of the polypeptide having a mismatch endonuclease activity in (d) of the method of inhibiting amplification of a nucleic acid having a specific nucleotide sequence in a nucleic acid amplification reaction may be determined by examining a concentration that does not inhibit DNA amplification reaction or a concentration effective for cleavage of a mismatched based pair in each reaction system as appropriate. The concentration of the oligodeoxynucleotide in (a) may be determined by optimizing the usage concentration while considering the amount of a template or amplification efficiency of the target DNA. For example, the concentration of the oligodeoxynucleotide can be 0.1 to 10 times the concentration of a primer used for amplification reaction.

The method of preferentially amplifying a target DNA may further comprise a step of detecting the amplified target DNA. This aspect of the present invention, as used herein, is sometimes referred to as "the detection method of the present invention". For example, according to the detection method of the present invention in which a DNA is used as a target to be detected, when a DNA that is not a target to be detected (a DNA having a specific nucleotide sequence) exists in an excessively large amount relative to a DNA that is a target to be detected (a target DNA), amplification of the non-target DNA as a template is inhibited by virtue of the oligodeoxynucleotide in (a) and the polypeptide having a mismatch endonuclease activity in (d) of the method of inhibiting amplification of a nucleic acid having a specific nucleotide sequence in a nucleic acid amplification reaction, and therefore the target DNA to be detected can be detected.

The detection method of the present invention enables to distinctively detect the wild-type and the mutant-type, for example, of a nucleic acid corresponding to a gene wherein a mutaion in the gene is known to be present. When the detection method of the present invention is performed using a DNA having a wild-type nucleotide sequence as the nucleic acid having a specific nucleotide sequence, a small number of a mutant allele can be detected in the presence of an excessively large amount of the normal allele (i.e., a DNA having the wild-type nucleotide sequence). For example, the method of the present invention is useful for detection of a circulating tumor DNA, or detection of a small amount of a fetal DNA sequence contained in the mother's blood. Examples of the mutation include microdeletion and point mutation. Polymorphisms generated by point mutation are called single nucleotide polymorphisms (SNPs). As used herein, a DNA having a mutant nucleotide sequence among SNPs is sometimes referred to as a DNA having a single nucleotide polymorphism mutation.

The nucleic acid having a specific nucleotide sequence may be preferably a nucleic acid containing at least one single nucleotide polymorphism selected from the group consisting of a single nucleotide polymorphism used as a tumor marker, a single nucleotide polymorphism correlating with a therapeutic effect of an agent for the treatment of cancer, and a single nucleotide polymorphism known to correlate with canceration of cells, but which the present invention is not particularly limited to. Examples of SNPs include those frequently found in tumor cells, and those known to correlate with a therapeutic effect of an agent for the treatment of cancer or carcinogenesis. Examples of such SNPs include SNPs of K-ras genes, B-raf genes, and epidermal growth factor receptor (EGFR) genes. Somatic mutations in the K-ras gene are frequently found in colorectal cancer, lung adenocarcinoma, thyroid cancer, and the like. Somatic mutations in the B-raf gene are frequently found in colorectal cancer, malignant melanoma, papillary thyroid cancer, non-small cell lung cancer, lung adenocarcinoma, and the like. Somatic mutations in the EGFR gene are frequently found in various solid tumors. It is known that the treatment of a cancer with an EGFR inhibitor such as gefitinib or erlotinib is likely to be effective when the EGFR gene in the cancer tissue has a specific single nucleotide polymorphism mutation. In contrast, it is known that a cancer is likely to be resistant to an EGFR inhibitor when the K-ras gene in the cancer tissue has a single nucleotide polymorphism mutation.

The detection method of the present invention may be performed using, as the material, a DNA obtained after treatment of a composition containing a methylated DNA extracted from an organism sample with bisulfite. According to the detection method of the present invention, detection of a small number of a methylated allele in the presence of an excessively large amount of a non-methylated allele, or detection of a small number of a non-methylated allele in the presence of an excessively large amount of a methylated allele can be performed.

As the treatment with bisulfite, a known bisulfite method which is used for detection of a methylated DNA can be used. By the treatment, non-methylated cytosine is changed into uracil, whereas methylated cytosine is not changed. When a reaction mixture treated with bisulfite is subjected to amplification by PCR, uracil is changed into thymine and methylated cytosine is changed into cytosine. In other words, detection of a small number of a methylated allele in the presence of an excessively large amount of a non-methylated allele at a specific site, and detection of a small number of a non-methylated allele in the presence of an excessively large amount of a methylated allele respectively correspond to examination of the presence of cytosine in the presence of an excessively large amount of thymine, and examination of the presence of thymine in the presence of an excessively large amount of cytosine. When amplification of an excessively large amount of DNA containing thymine or cytosine is inhibited, the presence of a small number of a methylated allele or non-methylated allele is easily examined.

For the step of detecting the target nucleic acid in the detection method of the present invention, electrophoresis, nucleotide sequence analysis, or real-time PCR using a probe such as a cycling probe or a TaqMan probe can be used. For these detection methods, conventional techniques can be directly used. In particular, use of a high resolution melting (HRM) analysis method allows amplification and detection of a DNA of interest by one step, and thus rapid and simple examination of the DNA of interest is attained.

EXAMPLES

The present invention will be more specifically explained by way of Examples, which the present invention is not limited to.

Preparation Example 1: Preparation of Genomic DNA

A genomic DNA of *Pyrococcus furiosus* was prepared following a method described in Example 1 of Japan Patent No. 3742659. Genomic DNAs of *Thermococcus barophilus* and *Methanocaldococcus jannaschii* were prepared following a method described in Example 8 of WO02/22831, except that *Thermococcus barophilus* and *Methanocaldococcus jannaschii* were used instead of *Thermococcus litoralis* as a microbial strain. These microbial strains are available from Deutsche Sammlung von Mikroorganismen und Zellkulturen GmbH.

Preparation Example 2: Preparation of Protein PF0012

(1) Preparation of pET-PF12, Plasmid for Expression of PF0012

For functional analysis of protein PF0012, a system for forced expression in *Escherichia coli* (*E. coli*) was constructed. For cloning the protein coding region (nucleotide numbers 11810-12610) of PF0012 gene from *Pyrococcus furiosus* shown in Genbank Acc. NC_003413 using In-Fusion (registered trademark) HD Cloning Kit (manufactured by TAKARA BIO INC.), two primers PF12F and PF12R were designed. The amino acid sequence of PF0012 is shown in SEQ ID NO:1. The nucleotide sequences of primer PF12F and PF12R are shown in SEQ ID NO:3 and SEQ ID NO:4 respectively. The genomic DNA from *Pyrococcus furiosus* as a template, these primers, and PrimeSTAR (registered trademark) HS DNA polymerase (manufactured by TAKARA BIO INC.) were used to amplify the region. The nucleotide sequence of the amplified region is shown in SEQ ID NO:5. The amplified fragment was inserted between NdeI and BamHI cleavage sites in plasmid pET15b (manufactured by Merck Millipore Corporation) using In-Fusion (registered trademark) HD Cloning Kit. The In-Fusion reaction mixture was used to transform *E. coli* JM109. From clones exhibiting ampicillin resistance, a plasmid for the expression of PF0012, pET-PF12 was isolated. From a crude extract of *E. coli* retaining this plasmid, a mismatch endonuclease activity was detected by a method described in Example 2. However, this plasmid was very unstable and caused internal deletion frequently. Thus the plasmid was not suitable for production of protein.

(2) Preparation of pET-optPFl2, Optimized Plasmid for Expression of PF0012

Since the expression of protein PF0012 using pET-PF12 was not stable, a nucleotide sequence was designed to encode the amino acid sequence of PF0012 by *E. coli* type codons, and a DNA containing the nucleotide sequence was artificially synthesized. The nucleotide sequence of this DNA is shown in SEQ ID NO:6. The DNA was digested with restriction enzymes NdeI and BamHI, and then purified. The DNA fragment thus obtained was inserted between NdeI and BamHI restriction sites in pET15b using DNA Ligation Kit <Mighty Mix> (manufactured by TAKARA BIO INC.). The ligation reaction mixture was used to transform *E. coli* JM109. Clones exhibiting ampicillin resistance were selected. From the clones, an optimized plasmid for the expression of PF0012, pET-optPF12 was obtained.

(3) Expression of Protein PF0012

*E. coli* BL21 DE3 was transformed with plasmid pET-optPF12. Clones exhibiting ampicillin resistance were isolated. Fresh single colony thus obtained was cultured in 2 ml of an LB medium containing 100 μg/ml of ampicillin (hereinafter, referred to as LB-AP medium) at 37° C. overnight. To 50 ml of an LB-AP medium, 500 μl of the overnight culture was added, and then cultured at 37° C. for 3 hours. Then, to the culture solution, IPTG was added at a final concentration of 1 mM, and then cultured at 37° C. for 3 hours. After completion of culture, the culture solution was centrifuged at 6000×g for 10 minutes to harvest bacteria cells from the culture solution.

(4) Purification of Protein PF0012

The bacteria cells described above were suspended in 3 ml of a solution containing 50 mM Tris-HCl, pH 7.5 and 100 mM NaCl (hereinafter, referred to as Buffer A), and subjected to ultrasonic disruption using VP-5S Ultras. Homogenizer (manufactured by TAITEC). After the ultrasonic treatment for 30 seconds was repeated 3 times, the suspension became transparent.

The suspension after the ultrasonic treatment was heated at 95° C. for 10 minutes to denature heat-labile protein, and then centrifuged at 17000×g for 10 minutes. A supernatant was collected. To the crude extract thus obtained, 500 μl of Ni-NTA Agarose (manufactured by QIAGEN) was added, followed by gentle stirring at 4° C. for 2 hours. The resin was filled into an Econo-Pac (registered trademark) column (manufactured by Bio-Rad Laboratories, Inc.), and washed with 20 ml of Buffer A containing 5 mM imidazole. After washing, 1 ml of Buffer A containing 300 mM imidazole was used to elute protein PF0012. An eluate was dialyzed with Buffer A at 4° C. two times, and then with Buffer A containing 50% glycerol at 4° C. overnight to obtain a solution containing protein PF0012.

Preparation Example 3: Preparation of PF0012 Homologous Proteins (1) Preparation of pET-TBA and pET-MJA, Plasmids for Expression of PF0012 Homologous Protein For the purpose of isolating PF0012 homologous proteins from two strains belonging to archaebacteria, *Thermococcus barophilus* and *Methanocaldococcus jannaschii*, regions encoding the protein were cloned. The amino acid sequences of PF0012 homologous proteins from these two strains are shown in SEQ ID NO:7 and SEQ ID NO:8 respectively.

From nucleotide sequence information shown in Genbank Acc. CP002372.1 and Genbank Acc. NC_000909.1, sequence information (TERMP_01877: nucleotide numbers 1674836-1675591, and MJ_0225: nucleotide numbers 215449-216240) corresponding to the PF0012 homologous proteins were obtained. Primers for cloning the corresponding genes were designed and prepared. For cloning of the TERMP_01877 gene, a pair of primers TBA1877F and TBA1877R were used. For cloning of the MJ_0225 gene, a pair of primers MJ255F and MJ255R were used. The nucleotide sequences of these primers are respectively shown in SEQ ID NOs:9, 10, 11 and 12.

The genomic DNA of *Thermococcus barophilus* or *Methanocaldococcus jannaschii* as a template, the above-mentioned primer pair, and PrimeSTAR (registered trademark) HS DNA polymerase (manufactured by TAKARA BIO INC.) were used to amplify the region. The nucleotide sequences of the amplified DNAs are shown in SEQ ID NOs:13 and 14. In the same manner as the preparation of pET-PF12 described above, the amplified DNAs each were inserted into plasmid pET15b to obtain plasmid pET-TBA and plasmid pET-MJA.

(2) Expression of PF0012 Homologous Proteins

The Expression and purification of the PF0012 homologous proteins were performed in the same manner as the expression of protein PF0012 described above, except that pET-TBA and pET-MJA were used as plasmids and after disruption of bacteria cell, the heat-labile proteins were precipitated by high-temperature treatment at 75° C. for 10 minutes. Thus PF0012 homologous proteins, TERMP_01877 and protein MJ_0225, were obtained.

Example 1: Preparation of Mutant PF0012 Protein (1) Preparation of pET-optPF12-W77F, Plasmid for Expression of Mutant PF0012

A gene encoding a mutant of protein PF0012 in which amino acid tryptophan (codon TGG) at position 77 in protein PF0012 (SEQ ID NO:1) was changed into phenylalanine (codon TTT) was prepared. The tryptophan at position 77 in PF0012 was believed to be an ssDNA binding region according to analysis of homologous protein NucS of protein PF0012 (The EMBO Journal, 2009, vol. 28, p. 2479-2489). The amino acid sequence of the mutant of PF0012 protein (hereinafter, referred to as mutant W77F) is shown in SEQ ID NO:2.

As primers for introduction of the mutation, mutF1 and mutR1 shown in SEQ ID NOs:15 and 16 were prepared. PCR was performed using pET-optPF12 as a template, the above-mentioned primers, and PrimeSTAR (registered trademark) Mutagenesis Basal Kit (manufactured by TAKARA BIO INC.). An amplification reaction mixture thus obtained was used to transform *E. coli* JM109. From clones exhibiting ampicillin resistance, a plasmid for the expression of mutant W77F, pET-optPF12-W77F was obtained.

(2) Expression and Purification of Mutant W77F

The Expression and purification of mutant W77F were performed in the same manner as those of wild-type protein PF0012 described above, except that pET-optPF12-W77F was used as a plasmid.

Example 2: Mismatch Cleavage Activity of Protein PF0012

(1) Preparation of Substrates for Measurement of Cleavage Activity—1

To determine the mismatch cleavage activity of protein PF0012, substrates for detection of the activity were prepared.

Two synthetic DNAs, one labeled with FAM at its 5' end and the other labeled with ROX at its 5' end were mixed and annealed to prepare the substrate. Four kinds of the ROX-labeled DNA: ROX-probe-G, ROX-probe-A, ROX-probe-T, and ROX-probe-C were synthesized. The nucleotide sequences of the four kinds of the ROX-labeled DNA are shown in SEQ ID NOs:17, 18, 19 and 20 respectively. The nucleotide sequences of ROX-probe-G, ROX-probe-A, ROX-probe-T, and ROX-probe-C were identical except for the 11th base from the 5' end, wherein the 11th bases are G, A, T, and C respectively. Four kinds of the FAM-labeled DNA: FAM-probe-G, FAM-probe-A, FAM-probe-T, and FAM-probe-C were synthesized. The nucleotide sequences of the four kinds of the FAM-labeled DNA are shown in SEQ ID NOs:21, 22, 23 and 24 respectively. The nucleotide sequences of FAM-probe-G, FAM-probe-A, FAM-probe-T, and FAM-probe-C were identical except for the 15th base (G, A, T, and C respectively) from the 5' end. From these, one kind of the ROX-labeled DNA and one kind of the FAM-labeled DNA were selected, mixed and hybridized to prepare the substrate for detection of the mismatch cleavage activity. The substrate is a double-stranded DNA forming base pairs at positions other than the 11th base from the base labeled with ROX and having one mismatched base pair at the position of the 11th base.

(2) Mismatch Cleavage Reaction by Protein PF0012 (Detection by PAGE)

A reaction mixture containing 1 µl of 5 µM one kind of the ROX-labeled DNA, 1 µl of 5 µM one kind of the FAM-labeled DNA, 1 µl of 10×Ex taq Buffer [attached with TaKaRa Ex Taq (registered trademark), manufactured by TAKARA BIO INC.], protein PF0012, and H$_2$O was prepared. Protein PF0012 and H$_2$O were added so that the total amount of the reaction mixture became 10 µl. After the reaction mixture was incubated at 60° C. for 1 hour, the reaction was stopped. The reaction mixture was subjected to electrophoresis on 10% polyacrylamide denaturing gel. After the electrophoresis, fluorescent signals in the gel were detected by FMBIO (registered trademark) (manufactured by Hitachi Solutions, Ltd.).

FIG. 1 a) shows detection of ROX signals. FIG. 1 b) shows detection of FAM signals from the same electrophoresis gel as the gel for detection of ROX signals. In the upper parts of the figures, the alphabets indicated to the left of ROX show the kinds of the used ROX labeled DNA, and specifically, G, A, T, and C show that ROX-probe-G, ROX-probe-A, ROX-probe-T, and ROX-probe-C were used respectively. The alphabets indicated to the left of FAM show the kinds of the used FAM labeled DNA, and specifically, G, A, T, and C show that FAM-probe-G, FAM-probe-A, FAM-probe-T, and FAM-probe-C were used respectively. The blank shows that the FAM labeled DNA was not used and only the ROX labeled DNA was used for the reaction.

In both systems, only when the substrate having a G-G, G-T, T-G or T-T mismatch was used, a fluorescent signal from a DNA which probably corresponded to a cleavage fragment was observed in a low molecular region. This fact shows that protein PF0012 recognizes the positions of G-G, G-T, T-G and T-T mismatches and has the ability to cleave both chains of the DNA in the vicinity of the mismatches.

Since the signal from the cleavage fragment did not show a smear pattern, protein PF0012 probably does not have exonuclease activity. In addition, when a single fluorescently labelled DNA was used, no fluorescent signal was observed in a low molecular region. Therefore, it was found that protein PF0012 has almost no activity of cleaving a single-stranded DNA.

It was found that protein PF0012 has selectivity for the bases of mismatches which the protein can cleave, high specificity for mismatches, and low reactivity to a double-stranded DNA forming normal base pairs and a single-stranded DNA. The high specificity for mismatches of protein PF0012 is advantageous when the protein is added to a nucleic acid amplification reaction, because the protein is less likely to inhibit the reaction by virtue of the high specificity for mismatches.

(3) Preparation of Substrates for Measurement of Cleavage Activity—2

To successively observe the mismatch cleavage activity of PF0012, substrates capable of generating a fluorescent signal by being cleaved were prepared.

DNAs of the nucleotide sequences shown in SEQ ID NOs:25, 26, 27 28 in which a quencher eclipse was bound to the 5' end and FAM was bound to the 3' end: DD-probe-G, DD-probe-A, DD-probe-T, and DD-probe-C were synthesized. As a template DNA for a complementary strand, template-G and template-T shown in SEQ ID NOs:29 and 30 were prepared. The fluorescently labeled DNA and the template DNA were mixed to prepare a double-stranded DNA substrate having a mismatched base pair at the position of the 5th base from the 5' end.

(4) Successive Observation of Mismatch Cleavage Reaction by Protein PF0012

A reaction mixture containing 1.5 µl of 5 µM the fluorescently labeled DNA (any one of DD-probe-G, DD-probe-A, DD-probe-T, and DD-probe-C), 1 µl of 25 µM template-G, 2.5 µl of 10×Ex Taq Buffer, protein PF0012, and H$_2$O was prepared. Protein PF0012 and H$_2$O were added so that the total amount of the reaction mixture became 25 µl. The reaction mixture was incubated at 55° C. for 1 hour, while a change in fluorescent intensity was observed once every minute. The reaction and fluorescent intensity were measured by using Thermal Cycler Dice (registered trademark) Real Time System (manufactured by TAKARA BIO INC.).

FIG. 2 shows the fluorescent intensity minute by minute. In the non-cleaved substrate, the fluorescent from FAM is quenched by eclipse. When the substrate is cleaved by protein PF0012, the distance between FAM and eclipse is increased and thus the fluorescent from FAM is observed.

In fact, only when the substrate containing a G-G or G-T mismatch was used, an increase in the fluorescent intensity was observed. When the substrate containing a G-A mismatch or a G-C base pairing was used, an increase in the fluorescent intensity was not observed. This experiment shows that protein PF0012 has the activity of cleaving mismatches comprised of G or T. The cleavage activity on each mismatched base pair is expressed as an initial rate at the time of reaction initiation, that is, a value calculated from a slope in a period maintaining linearity and correction by the fluorescent intensity of each substrate. When the reaction initial rates calculated form the curves shown in FIG. 2 are compared, it is found that the cleavage activity of protein PF0012 on G-G mismatches is 2 times higher than that on G-T mismatches.

Example 3: Mismatch Cleavage Activity of PF0012 Homologous Protein (1) Mismatch Cleavage Reaction by PF0012 Homologous Protein The mismatch cleavage activity and the base specificity of PF0012 homologous proteins from *Thermococcus barophilus* and *Methanocaldococcus jannaschii* were examined. The mismatch cleavage activity was observed on the basis of an increase in the fluorescent intensity as an indicator in the same manner as the successive observation of mismatch cleavage reaction by protein PF0012 except that the PF0012 homologous protein (protein TERMP_01877 or protein MJ_0225) was used as the enzyme protein.

As a result, as shown in FIG. 3, it is found that the proteins from *Thermococcus barophilus* and *Methanocaldococcus jannaschii* have the activity of cleaving mismatch positions comprised of G or T.

(4) Decrease of Error Rate in PCR Gene Amplification by Addition of Protein PF0012

Protein PF0012 can recognize a mismatched base pair in a double-stranded nucleic acid and cleave both strands of the double-stranded nucleic acid. This protein is heat-resistant and therefore can be added directly to a high-temperature reaction system such as PCR. The protein specifically cleaves double-stranded nucleic acids containing mismatched base pairs that are generated during PCR, and thereby occurrence of errors during the amplification reaction is expected to be inhibited.

(1) PCR with Addition of Protein PF0012

Protein PF0012 was added to a reaction mixture for PCR. The reaction mixture together with a genomic DNA of *Thermus thermophilus* HB8 as a template and four pairs of primers was subjected to PCR. The primer pairs used were Tth1F (SEQ ID NO:31) and Tth1R (SEQ ID NO:32); Tth2F (SEQ ID NO:33) and Tth2R (SEQ ID NO:34); Tth3F (SEQ ID NO:35) and Tth3R (SEQ ID NO:36); and Tth4F (SEQ ID NO:37) and Tth4R (SEQ ID NO:38). *Thermus thermophilus* HB8 Genomic DNA Solution (manufactured by TAKARA BIO INC.) as a template, the above-mentioned primer pairs and protein PF0012 were added. The PCR was performed using TaKaRa Taq (registered trademark) Hot Start Version (manufactured by TAKARA BIO INC.), in 30 cycles of 98° C. for 10 seconds, 55° C. for 30 seconds, and 72° C. for 1 minute.

(2) Calculation of Error Rate in PCR

DNA fragments amplified as described above were purified by using NucleoSpin (registered trademark) Gel and PCR Clean-up (manufactured by TAKARA BIO INC.). The DNA fragments were subjected to TA cloning in pMD19 (simple) plasmid (manufactured by TAKARA BIO INC.). Then, 96 plasmid clones for each amplified DNA fragment (384 clones in total) were subjected to nucleotide sequencing of the amplified regions.

After sequence information not containing the DNA of interest and sequence information presumed to be an error generated during the procedure for nucleotide sequencing analysis were removed, the nucleotide sequence of the amplified region was compared with the original genomic DNA sequence to count the number of different bases. The number of different bases was divided by the total number of analyzed bases to obtain an error rate.

In the DNA amplified by PCR without protein PF0012, 71 bp of 128826 bp were errors and the error rate was 0.055%. When PCR was performed with addition of protein PF0012, 28 bp of 97112 bp were errors and the error rate was 0.029%.

Thus, errors generated by nucleic acid amplification can be decreased by only addition of protein PF0012 to a PCR reaction mixture.

Example 5: Mismatch Cleavage Activity of Mutant W77F

Protein PF0012 originally has selectivity for mismatched base pairs comprised of G or T. We prepared an enzyme protein recognizing further limited mismatched base pairs by introducing a mutation into the protein.

(1) Successive Observation of Mismatch Cleavage Reaction by Mutant W77F

The mismatch cleavage activity and base specificity of mutant W77F prepared in Example 1 were observed by using the above-mentioned fluorescent DNA substrates. In this experiment, mutant W77F was used instead of protein PF0012, and DD-probe-G, DD-probe-T and template-G, template-T were combined. Other reaction conditions were the same as those in the measurement of successive mismatch cleavage activity described in Example 2(4).

As shown in FIG. 4, mutant W77F cleaved G-G mismatches well, whereas the cleavage activity on G-T mismatches was equal to or less than ½₀ of that on G-G mismatches and T-T mismatches were not cleaved. The activity of wild-type protein PF0012 on G-T mismatches was about ½ of that on G-G mismatches, as shown in FIG. 2. Thus, mutant W77F has more specific cleavage activity on G-G mismatches.

Example 6: Specific Amplification of a Very Small Amount of Contaminating Mutant Gene by Addition of Mutant W77F (1) Preparation of Template Plasmid For a mutated gene amplification test, plasmids as a template were prepared.

From sequence information of a human TP53 gene region shown in Genbank Acc. NG 017013, two primers shown in SEQ ID NOs:39 and 40: TP53CloneF and TP53CloneR were designed and synthesized. The region was amplified using the above-mentioned primers, a human genomic DNA (manufactured by Clontech Laboratories, Inc.) as a template, and PrimeSTAR (registered trademark) HS DNA polymerase. The nucleotide sequence information of the amplified region is shown in SEQ ID NO:41. The amplified DNA fragment was subjected to TA cloning in plasmid pMD19 (simple) (manufactured by TAKARA BIO INC.). A plasmid thus obtained was referred to as pTP53 (G). To change the 99th base G to A in the amplified region of the TP53 gene using pTP53(G) as a template, TP53AF and TP53AR shown in SEQ ID NO:42 and 43 were designed and prepared as primers for introduction of mutation. The plasmid pTP53(G) as a template, the primer pair for introduction of mutation, and PrimeSTAR (registered trademark) Mutagenesis Basal Kit were used to prepare mutant plasmid pTP53(A) in which G was changed to A at the desired position.

(2) Design and Preparation of Probe for Specific Mutant Gene Cleavage

An oligonucleotide for specific mutant gene cleavage was designed to have a sequence complementary to a region extending 8 bases in the 5' direction and 7 bases in the 3' direction from the position on pTP53(G) into which the mutation was introduced, and contain a mutation of C to G at a position corresponding to the mutation position on pTP53(G). When the oligonucleotide is hybridized with pTP53(G), a G-G mismatch is generated. To prevent an extension reaction from the oligonucleotide, a hydroxyl group at the 3' end of the oligonucleotide is replaced with an amino group. The oligonucleotide is referred to as an oligonucleotide for specific SNP cleavage, TP53deg. The nucleotide sequence of TP53deg is shown in SEQ ID NO:44.

(3) PCR with Suppressed Amplification of Specific Mutant Gene

Plasmid pTP53(G) alone, plasmid pTP53(A) alone, or a mixture of these plasmids as a template, mutant W77F, and TP53deg were used to perform PCR. The mixing ratios of the plasmids were, relative to 100 ng of pTP53(G), 100 ng (1/1), 10 ng (1/10), 1 ng (1/100), 100 pg (1/1000), and 10 pg (1/10000) of pTP53(A). A reaction mixture was prepared according to LightCycler (registered trademark) 480 High Resolution Melting Master (manufactured by Roche Diagnostics). The reaction mixture contained primers TP53AmpF and TP53AmpR shown in SEQ ID NO:45 and 46 respectively at a final concentration of 3 µM as primers for amplification, TP53deg at a final concentration of 3 µM as an oligonucleotide for specific mutant gene cleavage, and mutant W77F. Mutant W77F was added so that the total volume of the reaction mixture became 20 µl. PCR and fluorescent detection were performed by using LC480 (manufactured by Roche). The reaction conditions for PCR comprised prewarming at 95° C. for 5 minutes, 40 cycles of 3-step reaction consisting of 95° C. for 10 seconds, 95° C. for seconds and 72° C. for 20 seconds, finally as a dissociation reaction 95° C. for 1 minute, 40° C. for 1 minute, and then successive increasing temperature from 50° C. to 95° C., while fluorescent intensity at each temperature was observed. The same measurement was performed using a reaction mixture with no addition of mutant W77F.

(4) Detection of a Very Small Amount of Contaminating Mutant Gene

FIG. 5 shows amplification curves in the PCR. Table 1 shows Ct values calculated from the measurement results. When the reaction mixture did not contain mutant W77F, little change in the Ct value depending on the mixing ratio of the templates was observed. In contrast, when PCR was performed with addition of mutant W77F, the reaction using plasmid pTP53(G) alone as the template was inhibited and the Ct value was increased by 10 or more. This fact shows that mutant W77F inhibits DNA amplification from the plasmid by 1000 times or more. In the case of the amplification using plasmid pTP53(A) alone as the template, addition of mutant W77F hardly changed the Ct value, and the amplification was hardly inhibited by addition of mutant W77F. When the mixture of the plasmids was used as the template, amplifications depending on the amounts of pTP53(A) were observed. This fact shows that although mutant W77F cleaves a double-stranded nucleic acid containing a G-G mismatched base pair formed from pTP53(G) and TP53deg in the PCR reaction mixture, mutant W77F exhibits little cleavage activity on a G-A mismatched base pair formed from pTP53(G) and TP53deg. In addition, it was found that mutant W77F does not show amplification-inhibiting effect on a nucleic acid containing no mismatch. When the reaction mixture contained 1/10000 copies of pTP53(A) relative to pTP53(G), the Ct value was smaller than pTP53(G) alone. This suggests that the gene region of mutant-type (A) was specifically amplified from the template present in the reaction mixture at the mixing ratio of 1/10000 by virtue of mutant W77F.

TABLE 1

| | Ct value | |
|---|---|---|
| G:A ratio | No addition of mutant W77F | Addition of mutant W77F |
| 1:0 | 22.01 | 34.55 |
| 0:1 | 18.9 | 19.79 |
| 1:1 | 18.38 | 19.79 |
| 1:0.1 | 20.3 | 23.48 |
| 1:0.01 | 20.61 | 27.62 |
| 1:0.001 | 21.38 | 28.15 |
| 1:0.0001 | 21.22 | 32.71 |

The fluorescent intensity of each amplified product was measured while the temperature was increased from 50° C. to 95° C. to perform melting curve analysis. FIG. 6 shows graphs of first derivation of the fluorescent intensity at each temperature. As shown in FIG. 6 a), when the PCR was performed with no addition of mutant W77F, a peak appeared at 90.2° C. in the melting curve analysis of the amplified product using pTP53(G) alone as the template. When pTP53(A) was used alone as the template, a peak appeared at 89.6° C. In the case of a hetero-double strand in which both plasmids were present at the ratio of 1:1, in addition to the peaks appearing in the case of each plasmid alone, a broad peak appeared at around 88.5° C. Such differences of peaks in first derivation of melting curves can be utilized to distinguish the template containing wild-type (G) and the template containing mutant-type (A).

In the PCR with addition of mutant W77F, as shown in FIG. 6b), when the mixing ratio of plasmid pTP53(A) was 1/100 or more, the waveform was almost the same as that found in the case of using pTP53(A) alone as the template. This fact shows that only the amplification using pTP53(A) as the template was performed. When the mixing ratio of plasmid pTP53(A) was 1/1000 or 1/10000, the peak at 89.6° C. which probably came from pTP53(A) was observed, and further, the broad peak at around 88.5° C. which probably came from the hetero-double strand was also observed. This fact shows that in these mixing ratios, the fragment from pTP53(A) was preferentially amplified.

In this Example, it was found that the addition of a mutant of protein PF0012 and an oligodeoxyucleotide which generates a mismatch with the nucleotide sequence of the desired gene region leads to inhibition of amplification of the gene having the nucleotide sequence, and thus leads to specific amplification of a gene having a small amount of SNP.

INDUSTRIAL APPLICABILITY

The present invention is useful in broad fields including the fields of biotechnology, biology, medicine, and agriculture.

SEQUENCE LISTING FREE TEXT

SEQ ID NO:1; The amino acid sequence of PF0012 from *Pyrococcus furiosus*
SEQ ID NO:2; The amino acid sequence of PF0012 Y77F mutant
SEQ ID NO:3-4; A designed oligonucleotide primer for PCR
SEQ ID NO:5; The nucleic acid sequence of inserted DNA in the circular double stranded DNA for cloning PF0012 gene.

SEQ ID NO:6; The nucleic acid sequence of inserted DNA in the circular double stranded DNA for cloning a designed sequence deduced from PF0012 amino acid sequence.
SEQ ID NO:7; The amino acid sequence of TERMP_01877 from *Thermococcus barophilus*
SEQ ID NO:8; The amino acid sequence of MJ_0225 from *Methanocaldococcus jannaschii*
SEQ ID NO:9-12; A designed oligonucleotide primer for PCR
SEQ ID NO:13; The nucleic acid sequence of inserted DNA in the circular double stranded DNA for cloning TERMP 01877 gene.
SEQ ID NO:14; The nucleic acid sequence of inserted DNA in the circular double stranded DNA for cloning MJ_0225 gene.
SEQ ID NO:15-16; A designed oligonucleotide primer for PCR
SEQ ID NO:17-30; A designed oligonucleotide DNA for assay of a mismatch nuclease activity.
SEQ ID NO:31-40; A designed oligonucleotide primer for PCR
SEQ ID NO:41; The nucleic acid sequence of inserted DNA in the circular double stranded DNA for cloning partial TP53 gene.
SEQ ID NO:42-43; A designed oligonucleotide primer for PCR
SEQ ID NO:44; A designed oligonucleotide DNA for suppression of amplification of specific TP53 fragment
SEQ ID NO:45-46; A designed oligonucleotide primer for PCR

The invention claimed is:

1. A method of inhibiting amplification of a nucleic acid having a specific nucleotide sequence in a nucleic acid amplification reaction, the method comprising a step of performing the nucleic acid amplification reaction in the presence of the following (a) to (d):
  (a) an oligodeoxynucleotide which is designed to generate one to several mismatches when the oligodeoxynucleotide is hybridized with the nucleic acid having a specific nucleotide sequence or a complementary strand thereof;
  (b) a DNA polymerase;
  (c) at least one pair of oligonucleotide primers; and
  (d) a polypeptide having a mismatch endonuclease activity which is at least one polypeptide selected from the group consisting of the following (i) to (vi):
    (i) a polypeptide having an amino acid sequence of SEQ ID NO:1, 7 or 8;
    (ii) a polypeptide having an amino acid sequence which differs from the amino acid sequence of SEQ ID NO:1, 7 or 8 by substitution, deletion, insertion and/or addition of 1 to 10 amino acid residues, and having a mismatch endonuclease activity;
    (iii) a polypeptide having an amino acid sequence which shares at least 75% amino acid sequence identity with the amino acid sequence of SEQ ID NO:1, 7 or 8, and having a mismatch endonuclease activity;
    (iv) a polypeptide having an amino acid sequence of SEQ ID NO:2;
    (v) a polypeptide having an amino acid sequence which differs from the amino acid sequence of SEQ ID NO:2 by substitution, deletion, insertion and/or addition of 1 to 10 amino acid residues other than phenylalanine at position 77, and having a mismatch endonuclease activity; and
    (vi) a polypeptide having an amino acid sequence which shares at least 75% amino acid sequence identity with the amino acid sequence of SEQ ID NO:1, in which an amino acid residue corresponding to tryptophan at position 77 in the amino acid sequence of SEQ ID NO:1 is substituted with phenylalanine, and having a mismatch endonuclease activity.

2. The method according to claim 1, wherein the nucleic acid amplification reaction is a polymerase chain reaction (PCR) method or an isothermal nucleic acid amplification method.

3. A method of preferentially amplifying a target DNA, the method comprising inhibiting amplification of a DNA having a nucleotide sequence different from that of the target DNA in one to several nucleotides by the method according to claim 1.

4. The method according to claim 3, which is used for amplifying a DNA having a wild-type nucleotide sequence or the DNA containing a single nucleotide polymorphism mutation, wherein the amplification of the wild-type DNA and the amplification of the DNA containing a single nucleotide polymorphism mutation are distinguished from each other.

5. The method according to claim 4, wherein the single nucleotide polymorphism mutation correlates with canceration, or a therapeutic effect of an agent for the treatment of a cancer.

6. The method according to claim 3, wherein the DNA amplification reaction is performed by a polymerase chain reaction (PCR) method or an isothermal nucleic acid amplification method.

* * * * *